United States Patent
Eswaran et al.

(10) Patent No.: US 11,126,649 B2
(45) Date of Patent: Sep. 21, 2021

(54) SIMILAR IMAGE SEARCH FOR RADIOLOGY

(71) Applicant: Google LLC, Mountain View, CA (US)

(72) Inventors: Krishnan Eswaran, San Francisco, CA (US); Shravya Shetty, San Francisco, CA (US); Daniel Shing Shun Tse, Mountain View, CA (US); Shahar Jamshy, Santa Clara, CA (US); Zvika Ben-Haim, Haifa (IL)

(73) Assignee: Google LLC, Mountain View, CA (US)

( * ) Notice: Subject to any disclaimer, the term of this patent is extended or adjusted under 35 U.S.C. 154(b) by 146 days.

(21) Appl. No.: 16/032,276

(22) Filed: Jul. 11, 2018

(65) Prior Publication Data

US 2020/0019617 A1 Jan. 16, 2020

(51) Int. Cl.
*G06F 17/00* (2019.01)
*G06F 7/00* (2006.01)
(Continued)

(52) U.S. Cl.
CPC ............ *G06F 16/434* (2019.01); *G06F 17/18* (2013.01); *G06K 9/6215* (2013.01);
(Continued)

(58) Field of Classification Search
CPC ....... G06F 16/434; G06F 17/18; G16H 30/20; G16H 30/40; G06K 9/6215; G06T 7/0016;
(Continued)

(56) References Cited

U.S. PATENT DOCUMENTS

| | | |
|---|---|---|
| 5,733,721 A | 3/1998 | Hemstreet, III et al. |
| 6,789,069 B1 | 9/2004 | Barnhill et al. |

(Continued)

FOREIGN PATENT DOCUMENTS

WO 2019178322 A1 9/2019

OTHER PUBLICATIONS

Farugue, J. et al., "Content-Based Image Retrieval in Radiology: Analysis of Variability in Human Perception of Similarity", Journal of Medical Imaging, vol. 2(2) 025501, Apr.-Jun. 2015, pp. 1-9.
(Continued)

*Primary Examiner* — Pavan Mamillapalli
(74) *Attorney, Agent, or Firm* — McDonnell Boehnen Hulbert & Berghoff LLP

(57) ABSTRACT

A computer-implemented system is described for identifying and retrieving similar radiology images to a query image. The system includes one or more fetchers receiving the query image and retrieving a set of candidate similar radiology images from a data store. One or more scorers receive the query image and the set of candidate similar radiology images and generate a similarity score between the query image and each candidate image. A pooler receives the similarity scores from the one or more scorers, ranks the candidate images, and returns a list of the candidate images reflecting the ranking. The scorers implement a modelling technique to generate the similarity score capturing a plurality of similarity attributes of the query image and the set of candidate similar radiology images and annotations associated therewith. For example, the similarity attributes could be patient, diagnostic and/or visual similarity, and the modelling techniques could be triplet loss, classification loss, regression loss and object detection loss.

26 Claims, 10 Drawing Sheets

(51) Int. Cl.
| | |
|---|---|
| *G06F 16/432* | (2019.01) |
| *G16H 30/40* | (2018.01) |
| *G16H 30/20* | (2018.01) |
| *G06K 9/62* | (2006.01) |
| *G06T 7/00* | (2017.01) |
| *G06F 17/18* | (2006.01) |

(52) U.S. Cl.
CPC ........... *G06T 7/0016* (2013.01); *G16H 30/20* (2018.01); *G16H 30/40* (2018.01); *G06T 2207/10124* (2013.01); *G06T 2207/20084* (2013.01); *G06T 2207/30008* (2013.01)

(58) Field of Classification Search
CPC . G06T 2207/10124; G06T 2207/20084; G06T 2207/30008
USPC .......................................................... 707/758
See application file for complete search history.

(56) References Cited

U.S. PATENT DOCUMENTS

| | | | |
|---|---|---|---|
| 7,027,633 | B2 | 4/2006 | Foran et al. |
| 7,188,103 | B2 | 3/2007 | Furuhashi et al. |
| 7,353,224 | B2 | 4/2008 | Chen et al. |
| 8,199,994 | B2 | 6/2012 | Amir |
| 8,805,829 | B1 | 8/2014 | Zhou et al. |
| 9,053,386 | B2 | 6/2015 | Xue |
| 9,081,822 | B2 | 7/2015 | Xu et al. |
| 9,183,384 | B1 | 11/2015 | Bruhmuller |
| 9,275,456 | B2 | 3/2016 | Mori et al. |
| 9,495,388 | B2 | 11/2016 | Unay et al. |
| 10,134,131 | B1 | 11/2018 | Ando et al. |
| 10,146,914 | B1 | 12/2018 | Victors et al. |
| 10,281,456 | B1 | 5/2019 | Victors et al. |
| 10,467,754 | B1 | 11/2019 | Ando et al. |
| 10,769,501 | B1 | 9/2020 | Ando et al. |
| 2002/0111742 | A1 | 8/2002 | Rocke et al. |
| 2003/0013951 | A1 | 1/2003 | Stefanescu et al. |
| 2005/0209785 | A1 | 9/2005 | Wells et al. |
| 2006/0050946 | A1 | 3/2006 | Mitchison et al. |
| 2006/0204103 | A1 | 9/2006 | Mita et al. |
| 2007/0258630 | A1 | 11/2007 | Tobin et al. |
| 2009/0285466 | A1* | 11/2009 | Hipp ..................... G06T 7/0014 382/131 |
| 2010/0017389 | A1 | 1/2010 | Ogunbona et al. |
| 2010/0166266 | A1 | 7/2010 | Jones et al. |
| 2012/0158717 | A1* | 6/2012 | Unay ....................... G06F 16/50 707/728 |
| 2012/0242817 | A1 | 9/2012 | Pan |
| 2012/0250957 | A1* | 10/2012 | Syeda-Mahmood ........................ A61B 8/0883 382/128 |
| 2013/0116215 | A1 | 5/2013 | Coma et al. |
| 2015/0071541 | A1 | 3/2015 | Qutub et al. |
| 2015/0268822 | A1 | 9/2015 | Waggoner et al. |
| 2016/0364522 | A1 | 12/2016 | Frey et al. |
| 2017/0316286 | A1 | 11/2017 | Szegedy et al. |
| 2017/0344808 | A1* | 11/2017 | El-Khamy ......... G06K 9/00228 |
| 2017/0372224 | A1 | 12/2017 | Reimann |
| 2018/0084198 | A1 | 3/2018 | Kumar et al. |
| 2018/0089534 | A1 | 3/2018 | Ye |
| 2018/0260687 | A1 | 9/2018 | Kanno et al. |
| 2018/0314716 | A1 | 11/2018 | Kim et al. |
| 2018/0322660 | A1 | 11/2018 | Smith |
| 2018/0350067 | A1 | 12/2018 | Hamilton |
| 2019/0192880 | A1 | 6/2019 | Hibbard |
| 2019/0258925 | A1* | 8/2019 | Li ......................... G06F 16/583 |
| 2019/0304568 | A1 | 10/2019 | Wei et al. |

OTHER PUBLICATIONS

Korenblum, D. et al, "Managing Biomedical Image Metadata for Search and Retrieval of Similar Images", Journal of Digital Imaging, vol. 24, No. 4, Aug. 2011 pp. 739-748.
Nakayama, R. et al., "Potential Usefulness of Similar Images in the Differential Diagnosis of Clustered Microcalcifications on Mammograms", Radiology, vol. 253, No. 3, Dec. 2009, pp. 625-631.
Fornell, Dave, "How Artificial Intelligence Will Change Medical Imaging", Imaging Technology News, Feb. 24, 2017, https://www.itnonline.com/article/how-artificial-intelligence-will-change-medical-imaging, pp. 1-10.
Wang, J. et al., "Learning Fine-Grained Image Similarity With Deep Ranking", arXiv:1404.4661v1 [cs.CV], Apr. 17, 2017, pp. 1-8.
Gordo, A et al., "Deep Image Retrieval: Learning Global Representations for Image Search", arXiv.org 1604.01325v2 [cs.CV], Jul. 28, 2016, pp. 1-21.
Szegedy, C. et al., "Going Deeper with Convolutions", arXiv:1409.4842v1 [cs.CV], Sep. 17, 2014, pp. 1-12.
Szegedy, C. et al., "Rethinking the Inception Architecture for Computer Vision", arXiv:1512.00567v3 [cs.CV], Dec. 11, 2015, 10 pages.
Szegedy, C. et al., "Inception-v4, Inception-ResNet and the Impact of Residual Connections on Learning", Proceedings of the Thirty-First AAAI Conference on Artificial Intelligence, AAAI-17, vol. 4, 2017, pp. 4278-4284.
Sundararajan, Mukund et al., "Axiomatic Attribution for Deep Networks", arXiv:1703.01365v2 [cs.LG], Jun. 13, 2017, 11 pages.
Bahdanau, Dzmitry et al., "Neural Machine Translation by Jointly Learning to Align and Translate", Published as a Conference Paper on ICLR 2015, arXiv:1409.0473v7 [cs.CL], May 19, 2016, pp. 1-15.
Choi, Edward et al., "GRAM: Graph-Based Attention Model for Healthcare Representation Learning", arXiv:1611.07012v3 [cs.LG], Apr. 1, 2017, pp. 1-15.
Choi, Edward et al., "RETAIN: An Interpretable Predictive Model for Healthcare Using Reverse Time Attention Mechanism", arXiv:1608.05745v4, [cs.LG], Feb. 26, 2017, pp. 1-13.
Weston, J., "Learning to Rank Recommendations with the k-Order Statistic Loss", In Proceedings of the 7th ACM Conference on Recommender Systems, Oct. 12-16, 2013, 4 pages.
Litgens, G., et al. "A Survey on Deep Learning in Medical Image Analysis" arXiv:1702.05747v2 [cs.CV], Jun. 4, 2017, pp. 1-38.
Noel, Peter G. et al., Off-Site Smartphone vs. Standard Workstation in the Radiographic Diagnosis of Small Intestinal Mechanical Obstruction in Dogs and Cats, Vet Radiol Ultrasound. vol. 57, No. 5, 2016, pp. 457-461.
PCT International Search Report and Written Opinion, PCT International Application No. PCT/US2018/041557, dated Apr. 12, 2019, 19 pages.
Ah-Pine, Julien, "Data Fusion in Information Retrieval Using Consensus Aggregation Operators", 2008 IEEE/WIC/ACM International Conference on Web Intelligence and Intelligent Agent Technology, Dec. 9, 2008, pp. 662-668.
Wikipedia, "Metasearch Engine", https://en.wikipedia.org/w/index.php?title=Metasearch_engine&oldid=841525425, May 16, 2018, pp. 1-7.
Baeza-Yates R. et al., "Modern Information Retrieval, Chapter 5: Query Operations", Modern Information Retrieval, Jan. 1, 1999, pp. 117-139.
Schroff, Florian et al., "Facenet: A Unified Embedding for Face Recognition and Clustering", 2015 IEEE Conference on Computer Vision and Pattern Recognition (CVPR), IEEE, Jun. 7, 2015, pp. 815-823.
Wikipedia, "Regression Analysis", https://en.wikipedia.org/w/index.php?title=regression_analysis&oldid=751970896, Nov. 28, 2016, pp. 1-7.
Wikipedia, "Generalized Additive Model", https://en.wikipedia.org/wiki/generalized_additive_model, Jul. 19, 2016, 4 pages.
"Machine Learning in Cell Biology—Teaching Computers to Recognize Phenotypes"; Christoph Sommer, et al.; Journal of Cell Science, 126 (24), pp. 5529-5539; Nov. 2013.
"A Comparison of Machine Learning Algorithms for Chemical Toxicity Classification using a Stimulated Multi-scale Data Model"; Richard Judson, et al.; BMC Bioinformatics, 9:241; May 19, 2008.
"Enhanced CellClassifier: a Multi-class Classification Tool for Microscopy Images"; Benjamin Misselwitz, et al.; BMC Bioinformatics, 11:30; Jan. 14, 2010.

(56) References Cited

OTHER PUBLICATIONS

"Approaches to Dimensionality Reduction in Proteomic Biomarker Studies"; Melanie Hilario, et al.; Briefings in Bioinformatics, vol. 9, No. 2, pp. 102-118; Feb. 29, 2008.
"Automatic Identification of Subcellular Phenotypes on Human Cell Arrays"; Christian Conrad, et al.; Genome Research 14, pp. 1130-1136; Jun. 2004.
"Machine Learning and Its Applications to Biology"; Adi L. Tarca, et al.; PLoS Computational Biology, vol. 3, Issue 6, pp. 0953-0963; Jun. 2007.
"Pattern Recognition Software and Techniques for Biological Image Analysis"; Lior Shamir, et al.; PLoS Computational Biology, vol. 6, Issue 11, pp. 1-10; Nov. 24, 2010.
"Computational Phenotype Discovery Using Unsupervised Feature Learning over Noisy, Sparse, and Irregular Clinical Data"; Thomas A. Lasko, et al.; PLoS One, vol. 8, Issue 6, pp. 1-13; Jun. 24, 2013.
"Scoring Diverse Cellular Morphologies in Image-Based Screens with Iterative Feedback and Machine Learning"; Thouis R. Jones, et al.; PNAS, vol. 16, No. 6, pp. 1826-1831; Feb. 10, 2009.
"Analyzing Array Data Using Supervised Methods"; Markus Ringnér, et al.; Pharmacogenomics 3(3), pp. 403-415; May 2002.
"Development and Validation of a Deep Learning Algorithm for Detection of Diabetic Retinopathy in Retinal Fundus Photographs"; Varun Gulshan, et al.; JAMA 316(22), pp. 2402-2410; Nov. 29, 2016.
"Learning Fine-grained Image Similarity with Deep Ranking"; Jiang Wang, et al.; 2014 IEEE Conference on Computer Vision and Pattern Recognition (CVPR); Conference Dates: Jun. 23-28, 2014; Date Accessible Online: Sep. 25, 2014.
"Comparison of Methods for Image-based Profiling of Cellular Morphological Responses to Small-molecule Treatment"; Vebjom Ljosa, et al.; Journal of Biomolecular Screening 18(10), pp. 1321-1329; Sep. 17, 2013.
"FaceNet: A Unified Embedding for Face Recognition and Clustering"; Florian Schroff, et al.; 2015 IEEE Conference on Computer Vision and Pattern Recognition (CVPR); Conference Dates: Jun. 7-12, 2015; Date Accessible Online: Oct. 15, 2015.
"The Why and How of Phenotypic Small-Molecule Screens"; Ulrike S. Eggert; Nature Chemical Biology, vol. 9, No. 4, pp. 206-209; Mar. 18, 2013.
"When Quality Beats Quantity: Decision Theory, Drug Discovery, and the Reproducibility Crisis"; Jack W. Scannell, et al.; PLoS One 11(2); Feb. 10, 2016.
"Pipeline for Illumination Correction of Images for High-Throughput Microscopy"; Shantanu Singh, et al.; Journal of Microscopy; vol. 256, Issue 3, pp. 231-236; Sep. 16, 2014.
"High-Content Phenotypic Profiling of Drug Response Signatures across Distinct Cancer Cells"; Peter D. Caie, et al.; Molecular Cancer Therapeutics; vol. 9, Issue 6, pp. 1913-1926; Jun. 1, 2010.
"Annotated High-Throughput Microscopy Image Sets for Validation"; Vebjom Ljosa, et al.; Nature Methods 9(7); Published Online Jun. 28, 2012.
"Automating Morphological Profiling with Generic Deep Convolutional Networks"; Nick Pawlowski, et al.; bioRxiv preprint—http://dx.doi.org/10.1101/085118; Published Online Nov. 2, 2016.
"Visualizing Data using t-SNE"; Laurens van der Maaten, et al.; Journal of Machine Learning Research; vol. 9, pp. 2579-2605; Nov. 2008.
"Quantitative High-Throughput Screening: A Titration-Based Approach that Efficiently Identifies Biological Activities in Large Chemical Libraries"; James Inglese, et al.; vol. 103, No. 31, pp. 11473-11478; Aug. 1, 2006.
"Screening Cellular Feature Measurements for Image-Based Assay Development"; David J. Logan, et al.; Journal of Biomolecular Screening; vol. 15, No. 7; Jun. 1, 2010.
"Classifying and Segmenting Microscopy Images with Deep Multiple Instance Learning"; Oren Z. Kraus, et al.; Bioinformatics; vol. 32, No. 12, pp. i52-i59; Published Online Jun. 11, 2016.

"Increasing the Content of High-Content Screening: An Overview"; Shantanu Singh, et al.; Journal of Biomolecular Screening; vol. 19, No. 5, pp. 640-650; Apr. 7, 2014.
"Triplet Networks for Robust Representation Learning"; Mason Victors, Recursion Pharmaceuticals; DeepBio Video Conference hosted by the Carpenter Lab at the Broad Institute; Presented Sep. 28, 2016.
"Applications in Image-Based Profiling of Perturbations"; Juan C Caicedo, et al.; Current Opinion in Biotechnology, 39, pp. 134-142; Apr. 17, 2016.
"Data Analysis Using Regression and Multilevel/Hierarchical Models"; Andrew Gelman, et al.; Cambridge University Press New York, NY, USA, vol. 1; Jun. 13, 2012.
"Deep Learning"; Yann LeCUN, et al.; Nature, 521, pp. 436-444; May 28, 2015.
"A Threshold Selection Method from Gray-Level Histograms"; Nobuyuki Otsu; IEEE Transactions on Systems, Man, and Cybernetics, vol. SMC-9, No. 1, pp. 62-66; Jan. 1979.
"Scikit-learn: Machine Learning in Python"; Fabian Pedregosa, et al.; Journal of Machine Learning Research, 12, pp. 2825-2830; Oct. 2011.
"Is Poor Research the Cause of the Declining Productivity of the Pharmaceutical Industry? An Industry in Need of a Paradigm Shift"; Frank Sams-Dodd; Drug Discovery Today, vol. 18, Issues 5-6, pp. 211-217; Mar. 2013.
"Correlation Alignment for Unsupervised Domain Adaptation"; Baochen Sun, et al.; arXiv.1612.01939v1; retrieved from http://arxiv.org/abs/1612.01939; uploaded to arxiv.org on Dec. 6, 2016.
"How Were New Medicines Discovered?"; David C Swinney, et al.; Nature Reviews Drug Discovery, 10, pp. 507-519; Jul. 2011.
"Developing Predictive Assays: The Phenotypic Screening 'rule of 3'"; Fabian Vincent, et al.; Science Translational Medicine, vol. 7, Issue 293, pp. 293ps15; Jun. 24, 2015.
"Improving Phenotypic Measurements in High-Content Imaging Screens"; D. Michael Ando, et al.; bioRxiv preprint; retrieved from https://www.biorxiv.org/content/early/2017/07/10/161422.full.pdf; posted online Jul. 10, 2017.
"A novel scheme for abnormal cell detection in Pap smear images"; Tong Zhao et al.; Proceedings of SPIE, vol. 5318, pp. 151-162; 2004.
"From Cell Image Segmentation to Differential Diagnosis of Thyroid Cancer"; S. Ablameyko et al.; IEEE 1051-4651/02, pp. 763-766; 2002.
"Automated Classification of Pap Smear Tests Using Neural Networks"; Zhong Li et al.; IEEE 0-7803-7044-9/01, pp. 2899-2901;2001.
"Using CellProfiler for Automatic Identification and Measurement of Biological Objects in Images"; Martha S. Vokes, et al.; Current Protocols in Molecular Biology 14.17.1-14.17.12 (Apr. 2008).
"Strategy for Identifying Repurposed Drugs for the Treatment of Cerebral Cavernous Malformation"; Christopher C. Gibson, et al.; American Heart Association Journal—Circulation (Jan. 20, 2015).
"CellProfiler: Image Analysis Software for Identifying and Quantifying Cell Phenotypes"; Anne E. Carpenter, et al.; Genome Biology 2006, 7:R100 (Oct. 31, 2006).
"Quantifying Co-Cultured Cell Phenotypes in High-Throughput Using Pixel-Based Classification"; David J. Logan, et al.; Methods 96, 6-11 (Dec. 11, 2015).
"Cell Painting, a High-Content Image-Based Assay for Morphological Profiling Using Multiplexed Fluorescent Dyes"; Mark-Anthony Bray, et al.; Nature Protocols, 11(9): 1757-1774 (Aug. 25, 2016).
Olympus Life Science, Introduction to Confocal Microscopy, Dec. 31, 2014, Wayback Machine, file:///C:/Users/bbernardi/Documents/e-Red%20Folder/16133542/Confocal%29Microscopy%20-%20Introduction%20_%20Olympus%20Life%20Science.pdf, p. 1-11, (Year: 2014).
Sanjee Abeytunge, Evaluation of breast tissue with confocal strip—mosaiking microscopy: a test approach emulating pathology-like examination, Mar. 22, 2017, Journal of Biomedical Optics, p. 1-20. (Year: 2017).

(56) References Cited

OTHER PUBLICATIONS

Chetak Kandaswamy, High-Content Analysis of Breast Cancer using Single-Cell Deep Transfer Learning, 2016, Journal of Biomolecular Screening, vol. 21(3), p. 252-259. (Year 2016).
Juan C. Caicedo, Weakly Supervised Learning of Single-Cell Feature Embedding, Jun. 2018, IEEE/CVF Conference on Computer Vision and Pattern Rcognition, p. 9309-9318. (Year: 2018).
Juan C. Caidedo, Applications in image-based profiling of perturbations, Jun. 2016, Current Opinion in Biotechnology, p. 134-142. (Year: 2016).
Heba Sailem, Discovery of Rare Phenotypes in Cellular Images Using Weakly Supervised Deep Learning, 2017, IEEE International Conference on Computer Vision Workshops, p. 49-55. (Year: 2017).
Weakly Supervised Learning of Single-Cell Feature Embeddings Juan C. Caicedo, et al; available at https://doi.org/10.1101/293431; preprint uploaded to bioRxiv (biorxiv.org) on Apr. 2, 2018.
"Using Deep Learning to Enhance Cancer Diagnosis and Classification", Rasool Fakoor, et al; Conference Paper, Jun. 2013.

\* cited by examiner

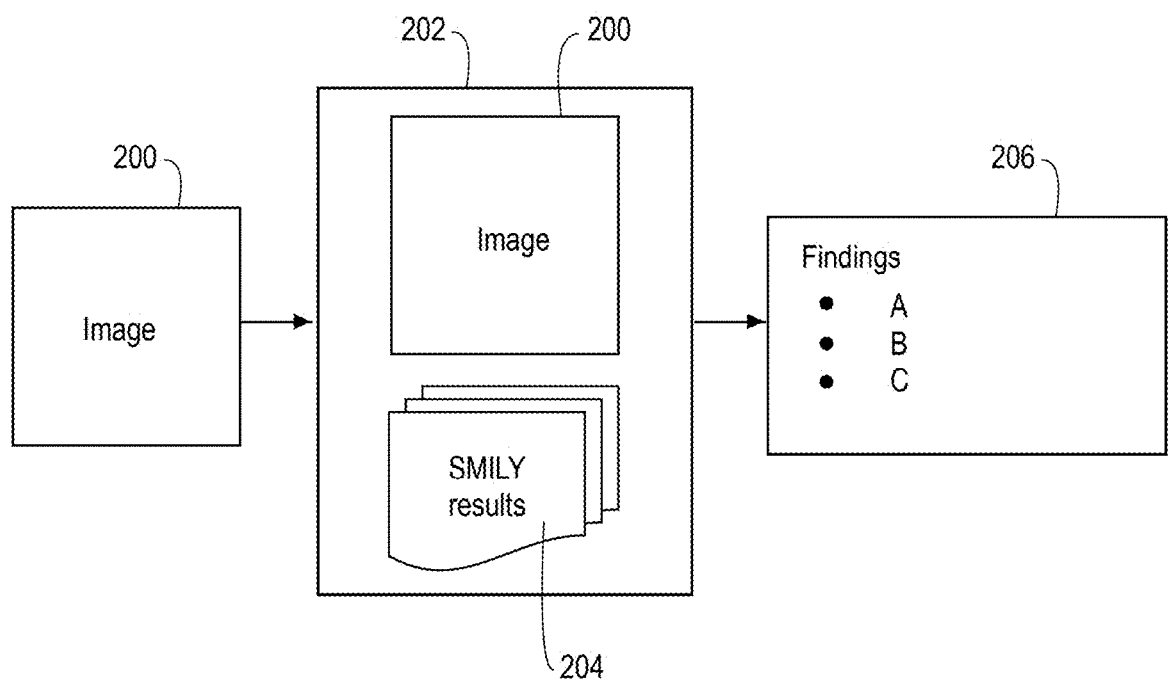

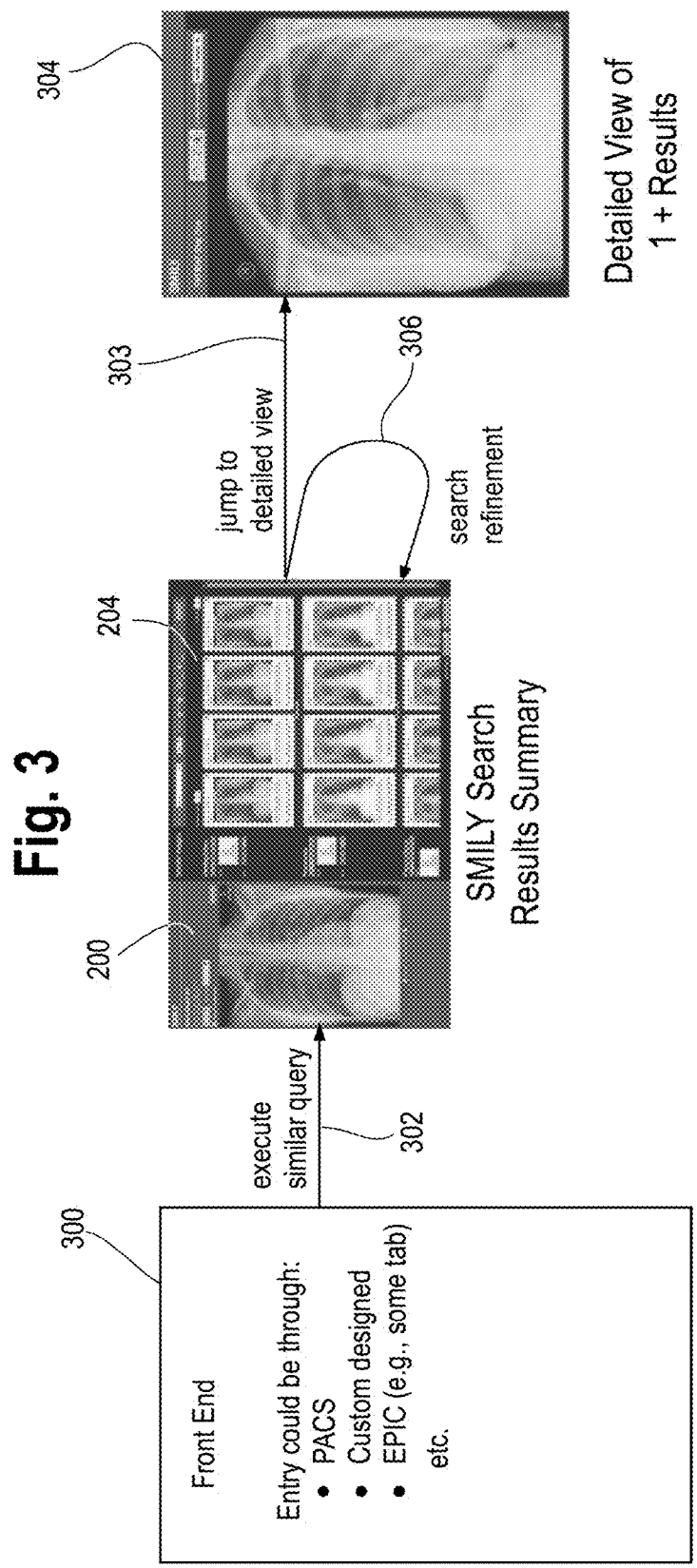

SIMILAR IMAGE SEARCH FOR RADIOLOGY

This disclosure relates to a method and system for identifying and retrieving similar radiology images to a query image.

BACKGROUND

There is a body of literature directed to machine learning methods for searching for similar images. See for example J. Wang, et al., *Learning fine-grained image similarity with deep ranking*, arXiv:1404.4661 [cs.CV] (2017), and the literature cited therein. See also U.S. Pat. Nos. 9,275,456, 9,081,822, 8,199,994, 7,188,103, and 7,027,633, and U.S. patent application publications 2012/0242817, 2010/0017389, 2007/0258630, and 2003/0013951. One of the problems that is faced in similar image search in the present context, i.e., searching for similar radiology images, e.g., chest X-rays, is defining similarity. Visual similarity alone between two images is generally not sufficient in and of itself to be clinically useful, e.g. to provide an aid in diagnosis. To appreciate this, it helps to understand how radiology imaging information is organized. One can organize a multi-stage hierarchy of medical images with heterogeneous annotation data. Such a hierarchy is shown in FIG. 1A. At the highest level of the hierarchy are the patients associated with the images. Within a patient, one can further subdivide the images into different cases. Within each case, one can further subdivide the images into a spatial orientation called a stack, which corresponds to the orientation of images according to some form of Cartesian alignment, e.g. along a plane corresponding to each axis in three dimensions (this is how computed tomography (CT) images are organized). Within each stack, one finds the images ordered based on their position within a stack. Finally, at any of these levels, there are associated heterogeneous annotations, including a mix of enumerated classes (e.g., presence or a medical condition like pneumonia), numeric data (e.g. age, weight, body mass index, etc.), and free text (e.g. radiology reports), and other metadata.

Note that the deep nesting of this hierarchy, as shown in FIG. 1A, is different from what one might find in e.g. a YouTube video. While the slices of a CT within a stack might resemble the image frames of a video, the addition of other dimensions are an important additional complication. Whereas videos can have regularly sampled frame rates (e.g. 30 frames per second), the temporal nature of medical data is different in that the sampling rate is often not fixed and in many cases irregular. For instance, while a patient might get daily chest X-rays in an ICU, the frequency of X-rays might be considerably less frequent if they are transferred to a different hospital, or are discharged, and return several weeks later.

Therefore, in order for similar image search in radiology to be clinically useful, one of the problems that needs to be solved is how to work with irregularly sampled, multi-level hierarchical images with heterogeneous annotations/metadata.

In addition to the distinction that such radiographic imagery (chest X-rays, CTs, mammograms, ultrasound, etc.) are organized in a manner that make them materially different from the images and video one might find on Google Image Search or YouTube, respectively, what constitutes similarity is subject to context.

Within the problem domain of retrieving similar medical images, the reference information returned is useful only if it provides the clinician with medically relevant information for the decision they are trying to make. Thus, for example, for a person trying to identify whether a 21-year old female should get a follow-up CT given a chest X-ray that contains a pulmonary nodule or mass (something that would require a follow up), returning chest X-ray results of 21-year-old females without any nodules or masses are not as useful as returning chest X-rays with nodules and masses. Thus, one of the main challenges is to define a metric of similarity that is contextually tailored to the relevant clinical decisions being supported by a similar image search tool.

The work described in this document also reflects awareness that medical similarity, particularly clinically useful similarity, is different from medical classification. While one might consider classification to be a simple way to address the medically specific nature of similarity, note that the problems of classification and similarity are not the same thing. Consider a simplified example of two different feature representations of a linear classifier, with reference to FIG. 1B. While it is possible to build classifiers that both perfectly classify the positive and negative cases, but in one classifier, indicated by the illustration 100 on the left of FIG. 1B, each positive example (indicated by the + sign) has a corresponding negative example (illustrated by the − sign) that it is closer to than it is to other positive examples, whereas in another classifier, indicated by the illustration 102 on the right of FIG. 1B, all positive examples are closer to one another than they are to any negative examples. This simplified example gets even more complicated as one considers similarity on multiple dimensions of annotated information combined with the temporal and spatial components of radiographic medical information described above in the context of FIG. 1A. Thus, it is not sufficient to be able to capture features that help determine decision boundaries between classes. Rather, the features themselves need to cluster images within the same class closer to one another, as illustrated in the right hand example of FIG. 1B.

The present system for identifying and retrieving similar medical radiology images is motivated by several needs. One is that, in addition to radiologists, other medical practitioners like emergency room doctors may need to read radiographs. Radiologists may be more familiar with how certain conditions look than others based on what they've seen previously. Additionally, the distribution of cases can vary from one hospital to another. For instance, tuberculosis might be more prevalent in hospital A and quite rare in hospital B. There exists a long tail of rare conditions for which a high number of positives might be difficult to isolate for classification.

SUMMARY

This document proposes a solution to these issues by means of a system that features a combination of back-end design (software infrastructure), including fetchers and scorers, and modelling techniques implemented in the scorers which generate a similarity score that captures a plurality of similarity attributes (e.g., diagnostic, visual and patient) of the query image and a set of candidate similar radiology images, and the annotations (e.g., metadata or medical reports) associated therewith.

In particular, the system includes one or more fetchers receiving the query image and retrieving a set of candidate similar radiology images from a data store in the form of a library of ground truth annotated reference radiology images. The fetcher can take the form of a trained deep convolutional neural network, nearest neighbor algorithm based on a feature vector extracted from the image, or classifier. These candidate images may or may not already be associated with scores. For example, in one possible configuration, if the query images are already indexed, scores to similar images may be pre-computed and cached, and the fetcher may make use of pre-cached similar images to retrieve candidate similar images.

The system further includes one or more scorers which receive the query image and the set of candidate similar radiology images and generate a similarity score between the query image and each candidate image. The score can be computed for example based on pre-computed embedding and a standard distance metric (e.g., cosine or Euclidean distance) in an embedding space. For example, the scorer looks up the embedding of an image in a database and then uses a distance measure in the embedding space to determine how similar the query image is to the candidate similar radiology images.

The system further includes a pooler which receives the similarity scores from the one or more scorers, ranks the candidate images (e.g., on the basis of acuteness/severity), and returns a list of the candidate images reflecting the ranking.

The scorers implement a modelling technique to generate the similarity score that can capture similarity on many different attributes or axes (e.g., diagnostic, visual, patient, etc.). Diagnostic, visual and patient attributes are some of the many signals that could be important on specific axes of similarity, but these three are not meant to be an exhaustive list. A number of different modelling techniques are contemplated, and in a typical implementation where there are more than one scorer they will each use a different modelling technique that captures these different attributes of similarity (e.g., diagnostic, visual and patient).

Additionally, the fetcher can also use these different modelling techniques to retrieve similar medical images from the data store. In particular, there is an interplay in how one fetches or selects the initial images to score and rank and the models that are used. For example, if the system is configured as a tool to return similar images that are positive for a particular condition such as pneumothorax, and we are confident that the query image is classified as positive for pneumothorax, we could fetch just the images that we know are positive for pneumothorax (since the reference images in the data store have ground truth annotations) and use them for scoring by the scorers and subsequent ranking. In this case, the fetcher would run a model to make an inference about the state of the query image, and use that to filter the candidate images that are sent for scoring.

Some of the modelling techniques include triplet loss, classification loss, regression loss, and object detection loss. Attention models may also be used which takes into account the additional regional information within an image, which allows us to consider one additional layer of hierarchy of the regions of interest within an image, i.e., sub-image level metadata.

As will be explained below, triplet loss is a technique that handles heterogeneous data consistently in a way that notionally captures similarity. Specifically, suppose we have three images: a query image and two candidate images. If we know that we have a query image that is closer to one of the candidate images (the positive) than it is to the other (the negative), then we expect the distance between the extracted features between the positive pair (query and positive candidate) to be smaller than the distance between the query and negative candidate. The triplet loss is thus the difference between these two distances. The present document describes a variety of methods of calculating triplet loss (i.e., a distance metric between a query image and two candidate images), including patient and clinical metadata (including numerical data, e.g., BMI, age, weight, etc.), structured labels, a Hamming distance over a vector of classification labels based on medical reports, and the location of abnormalities within an image. As noted other modelling techniques for determining similarity are also contemplated, and in one possible configuration the scorers each use a different modelling technique.

The general arrangement of fetchers, scorers, and a pooler allows for the processing and retrieving of similar radiology images on a scalable basis. Further, the use of different modelling techniques for similarity in the fetching and scorers allows for different aspects of similarity modelling to be combined to generate a set of similar medical images that provide diagnostically useful information to a user and that meet the needs of clinical applications of similar medical image search, particularly in the radiology context.

In one configuration, the information that is returned to a user after performing the fetching, scoring and ranking of the similar images includes not just the similar images (and associated metadata), but also information that can be culled, inferred or aggregated from the result set of the similar images. Accordingly, the system includes a processing unit which performs the aggregation or inferring of data from the candidate similar images. Several examples are as follows.

1) The images can be returned not merely as a list of images but rather grouped together across common attributes that are useful for supporting a clinical decision. For example, images with certain misplaced foreign bodies (e.g., misplaced nasogastric tube) might be grouped separately from those images that are associated with a diagnosis of pneumothorax.

2) The groupings can involve the aggregation of relevant common text from radiology free text reports. For example, while there may not be a specific label indicating that an endotracheal tube is misplaced, we can aggregate together images that are associated with reports having common phrases that imply this condition to be present, for example reports having text entries "endotracheal tube at the level of the carina", "endotracheal tube tip terminates in right main bronchus", or "ET tube tip could be advanced a couple of centimeters for standard positioning."

3) When we group by these common phrases in reports (or by the presence or absence of enumerated conditions in other metadata), as in example 2) above, we can aggregate these into values and compare them against a baseline, and report the comparison, e.g., as a statistic. For example, if the similar image results are 100 images, and we may report that fact that 60 of the 100 images indicated pneumothorax was present, even though only 1 of every 1000 images in the database (reference library) contain pneumothorax.

Accordingly, once the set of similar images have been identified, relevant information is returned to the user from this set. This would normally include not only the images themselves, but also metadata associated with each of these images like radiology reports, clinical decisions made (e.g., prescribing of antibiotics, diuretics), classification diseases/conditions associated with the similar image, and information or statistics relating to a grouping/aggregation of these results. That aggregation could include clustering together image results with similar properties, generating pivot tables summarizing the prevalence of certain conditions/diagnoses in the images, as well as indicating the prevalence of common phrases within the radiology reports. Note that these aggregations can also be based on future outcomes for a given patient.

It will be appreciated that the fetchers, scorers and pooler are configured to perform the various functionality described above.

In another aspect, a method is disclosed for identifying and retrieving similar radiology images to a query radiology image. The query image is associated with annotations including metadata. The method includes a step a) of curating (i.e., developing and storing) a data store of ground truth annotated radiology images, each of the radiology images associated with annotations including metadata. The method includes a step b) of receiving the query image and retrieving a set of candidate similar radiology images from the data store. The method includes a step c) of generating a similarity score between the query image and each candidate similar radiology image using at least two different scorers. The at least two scorers implement a different modelling technique to generate the similarity score capturing a plurality of similarity attributes of the query image and the set of candidate similar radiology images and the annotations associated therewith.

In one embodiment, the method includes a step d) of ranking the candidate similar radiology images and a step e) of returning a list of the candidate similar radiology images reflecting the ranking and aggregated information obtained from the annotations associated with the set of candidate similar radiology images.

BRIEF DESCRIPTION OF THE DRAWINGS

FIG. 2 is an illustration of a use case of the methods of this disclosure in which similar medical images to a query image are retrieved and used by a medical professional, e.g., radiologist or pathologist, to make certain findings regarding a patient associated with the query image.

FIG. 3 is a high level illustration of the workflow using the methods of this disclosure from a user perspective.

DETAILED DESCRIPTION

Figure 1A:
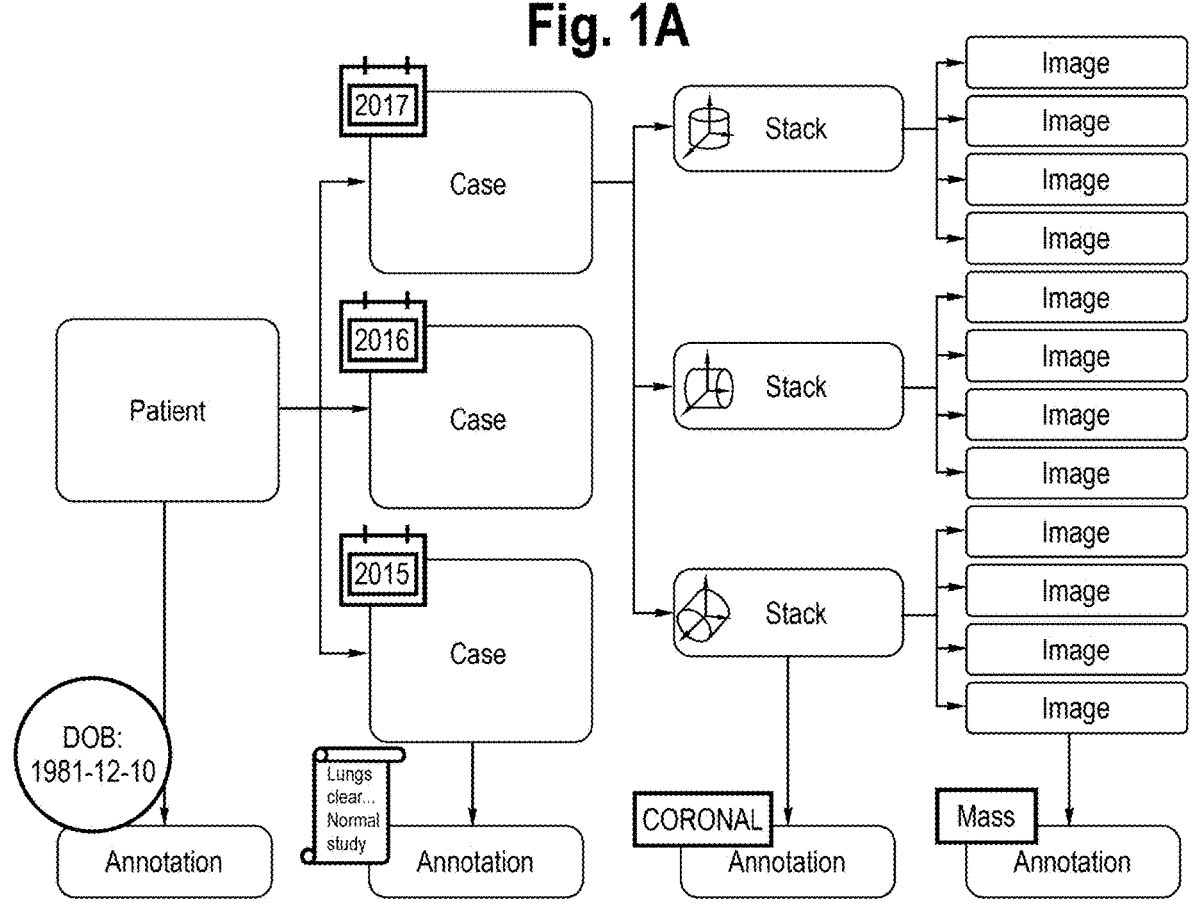
FIG. 1A is an illustration of a multi-stage hierarchy of medical information along with associated heterogeneous annotation data.

This document describes a computer-implemented system for identifying similar radiology images to a query image. The system can be considered a tool for assisting a medical professional such as a radiologist, ER doctor, or primary care physician in arriving at a diagnosis for a patient based on a radiology image of the patient, such as a chest X-ray, mammogram, or CT scan. The system provides diagnostically useful output information to a user based upon an input image.

The general idea of how the system works is illustrated in FIG. 2. A radiology image 200 is obtained, e.g., using conventional imaging equipment, and supplied to the system 202 of this disclosure. The image 200 is considered the query image; that is, the medical professional seeks to find similar images to the image 200. The query image 200 is associated with medical information, metadata, reports, etc. (collectively "annotations"). The system 202 returns a list of results 204 in the form of similar radiology images (SMILY, "similar medical image like yours") obtained from a data store in the form of a reference library of ground-truth annotated radiology images of the type of the query radiology image 200. The results 204 will include not only the similar images but also the annotations associated therewith. The results will generally also be returned along with groupings and aggregated information, e.g., statistics, as will be explained in detail in FIGS. 3 and 8-10 later in this document. The medical practitioner then reviewing the query image 202 and the results 204 enters findings 206, typically diagnostic findings, in the medical record of the patient, for example in the form of a free-text report or structured note. One goal of the system of this disclosure is provide a tool to improve the decision-making task; the medical professional uses the results in addition to other diagnostic procedures and methods to generate the clinical findings. Note that all findings for an image may not be clinically relevant to a specific action/plan; here, we are referring in FIG. 2 to findings A, B and C as those findings that are clinically relevant.

Figure 4:
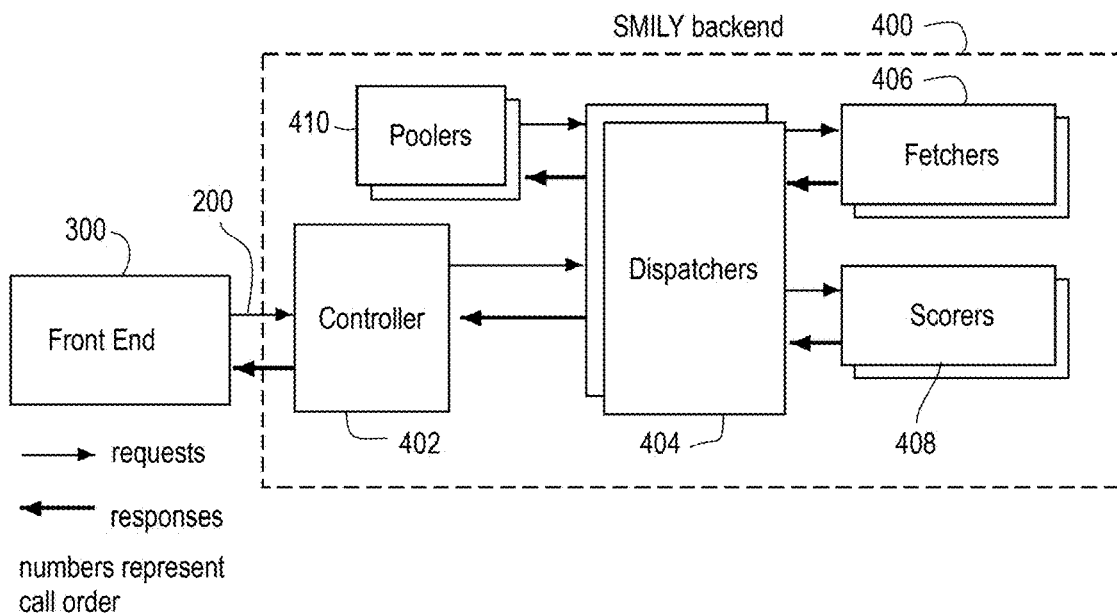
FIG. 4 is a block diagram of one possible configuration of a back-end design receiving a query image, and including a fetcher fetching candidate images, a plurality of scorers, and a pooler which receives the similarity scores from the scorers, ranks the candidate images (e.g., on the basis of acuteness/severity), and returns a list of the candidate images reflecting the ranking.

FIG. 3 illustrates the method of operation of the system from a user perspective. As indicated in FIG. 3, there is a front end component 300 which provides a user interface to the medical professional on a conventional computer workstation (not shown). The front end component is entered from a PACS (picture archiving and communications) system, such as by activating a tab or icon within the PACS system, or which may be a custom design. The front end component provides a software interface, e.g., via a set of application programming interfaces (APIs) to a back end system in the form of a set of computer software modules which are shown in FIG. 4, executing within a computer system that may be either local to the clinician or in a remote, cloud computing environment. The front end component provides options for a user to select a query image. The system executes a similar image search to the query image, as indicated at 302. The front-end system provides a display on the workstation of the query image 200 and the results 204. The results are shown in a summary format in FIG. 3, but a variety of other formats are described later in conjunction with FIGS. 8-10 and the details may vary from that shown in FIG. 3. The user has the option to click or select any one of the similar images in the results 204 (indicated by the arrow 303) and a detailed view of the similar image 304 that was selected is displayed. The interface of the front end component also includes tools to refine the search (indicated by the arrow 306) and similar images are retrieved based on the refinements that are specified. Such refinements could be specified by entry of text in a text box, by selecting only patients by certain age groups, smoker status, sex, diagnosis, or other criteria, or by selecting only a set of images associated with a particular diagnosis or condition.

Once the set of similar radiology images have been identified, relevant information is returned to the user from this set. This would normally include not only the images themselves, but also metadata associated with each of the images like radiology reports, clinical decisions made (e.g., prescribing of antibiotics, diuretics), classification diseases/conditions associated with the similar image, an information relating to a grouping/aggregation of these results. That aggregation could include clustering together image results with similar properties, generating pivot tables summarizing the prevalence of certain conditions/diagnoses in the images, as well as indicating the prevalence of common phrases within the radiology reports. Examples of these kinds of aggregations will be explained later in this document.

FIG. 4 is a block diagram of one possible configuration of a back end 400 in the form of a set of software modules or objects which receive a query image and generate a list of results. The software modules are executed in a computer system having computing resources and processing units, e.g., a graphics processing unit, memory storing parameters of machine learning models, processing unit for calculating statistics, etc. as will be appreciated by those skilled in the art. The flow of requests and response are indicated by the thin and thick arrows as indicated by the legend in FIG. 4.

The objects in the back end can be roughly divided into two categories:

(a) Objects that control the state machine of the back end 400:

Controller 402: an object that receives queries from outside the back end (e.g., the front end 300 of FIG. 3) and orchestrates the Dispatchers 404, Fetcher 406 and Pooler 410 to generate a list of similar image results and ranking the results. The controller also constructs these objects from a configuration or initial state.

Dispatcher 404: an object that distributes a query between several different fetchers 404 and scorers 406, then collates the results using a pooler 410. The dispatcher sends the candidate images and the queried image to a set of scorers in parallel, fetches the results, and passes the resulting scores to the pooler 410 for ranking.

(b) Objects that perform specific operations required to identify and retrieve the similar images:

(1) Fetcher(s) 406—an object that receives a query image 200 and generates a set of candidate similar images by querying a data store (not shown in FIG. 3) in the form of a library of ground truth annotated reference images, which may or may not already be associated with scores. In one embodiment, there can be two or more fetchers each using different modelling techniques to retrieve a set of candidate similar radiology images.

(2) Scorer(s) 408—an object that receives a query image and a set of candidate images and returns a similarity score between the query image and each candidate image. In preferred embodiments, there are two or more scorers. As will be explained below, the scorers implement a modelling technique to generate the similarity score capturing a plurality of similarity attributes of the query image and the set of candidate similar radiology images and annotations associated therewith, such as diagnostic, visual and patient similarity. If there are multiple scorers, each implements a different modelling technique.

(3) Pooler 410—an object that receives scoring results from several different scorers or fetchers, collated by the dispatcher 404, and returns a single list of the combined results. The pooler ranks the candidate images (e.g., on the basis of acuteness/severity), and returns a list of the candidate images reflecting the ranking.

The software architecture of FIG. 4 provides the ability to combine different scoring techniques trained from different models together and combine them to produce a final ranking in a scalable manner.

Figure 5:
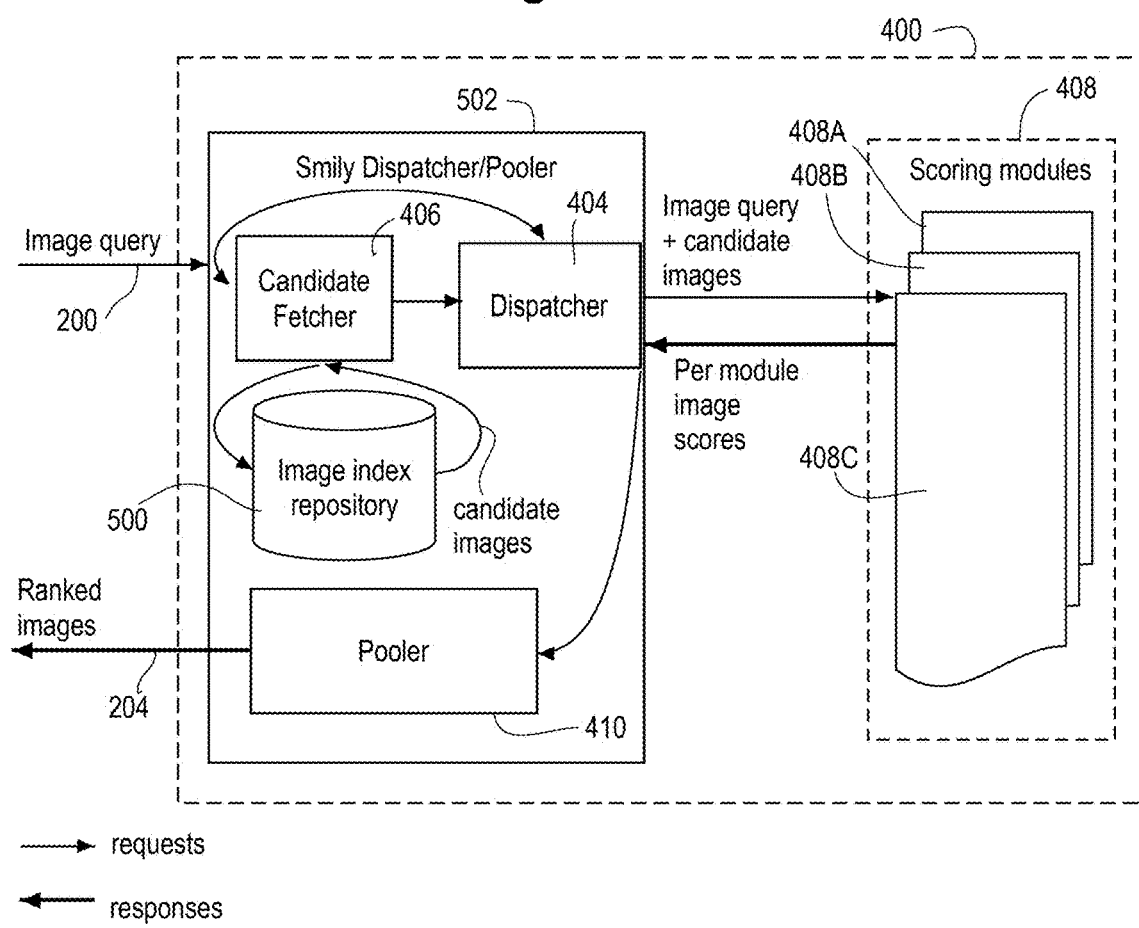
FIG. 5 is a block diagram of another possible configuration of a back-end design of FIG. 4.

The software architecture of FIG. 4 can be realized in other formats and arrangements of the basic building blocks or objects. FIG. 5 illustrates one possible variation. In this configuration the query image 200 is received by a dispatcher/pooler 502 which includes a fetcher 406 which retrieves a candidate set of similar images from a data store or repository 500. The set of images is sent to a dispatcher 404 which sends the image query and the candidate images to a scoring module 408 which includes three different scorers 408A, 408B and 408C. Each module 408A, 408B and 408C uses a different modelling technique to generate the similarity score for the candidate images. These modelling techniques each capture or take into account two or more similarity attributes between the query image and the set of candidate similar radiology images, and the associated annotations, such as patient, diagnostic, and visual similarity. These attributes of similarity can be represented as coordinate axes in a multidimensional embedding space, see FIG. 11, where feature vectors of the image and associated annotations are used to plot the position of the query image and the candidate set of similar images in this feature space, and distance metrics or other types of modeling techniques described below are then used to generate similarity scores reflecting the similarity.

The similarity scores and candidate set of similar images are then returned to the dispatcher 404 and then supplied to the pooler 410, which then ranks the candidate set of similar images using the scores. The pooler then returns the ranked images as results 204 (again, preferably with aggregation information, statistics, groupings, metadata, etc. as described in detail elsewhere).

Figure 6:
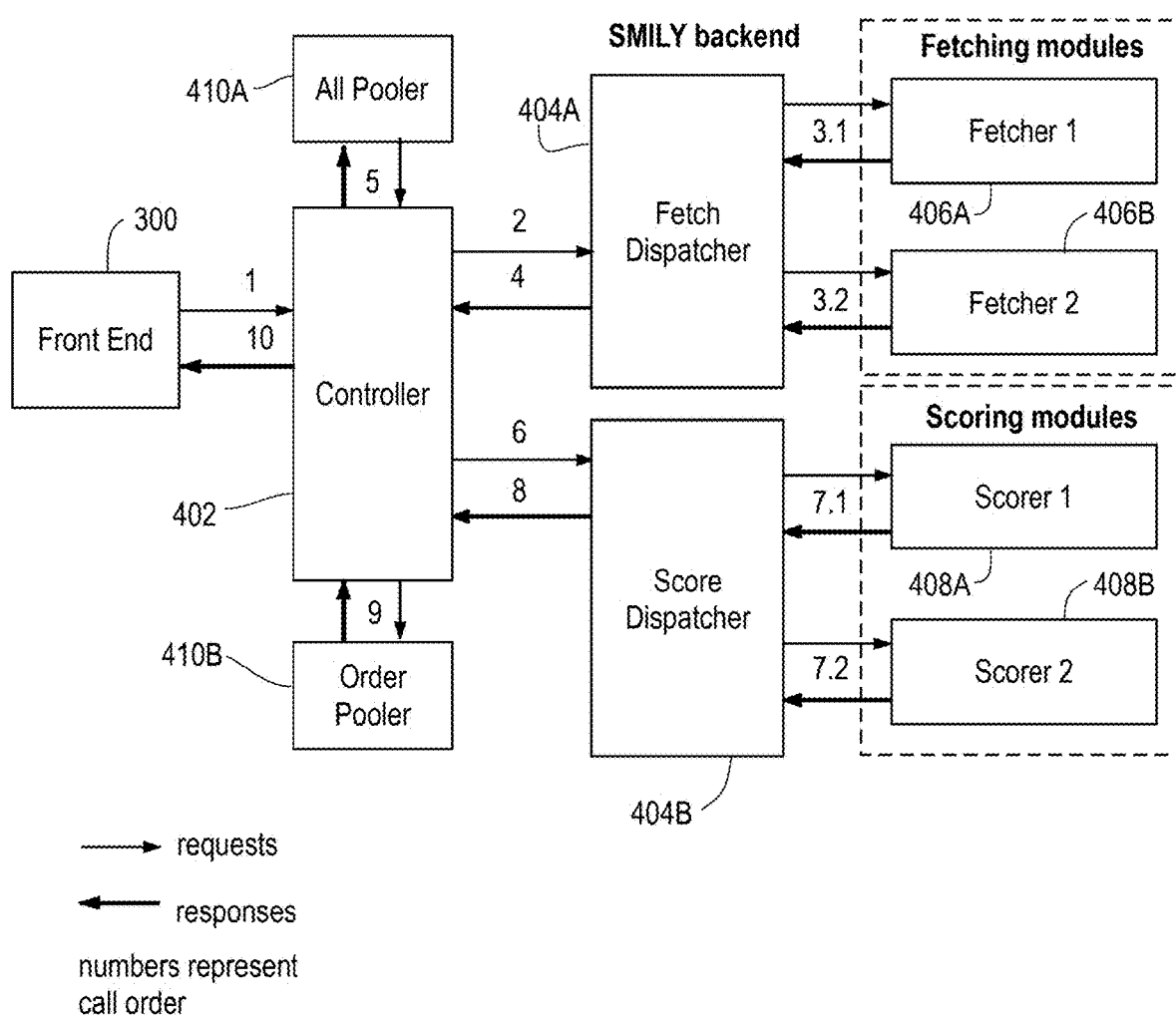
FIG. 6 is a block diagram of another possible configuration of a back-end design of FIG. 4.

FIG. 6 illustrates another possible configuration. The numbers 1, 2, 3.1, 3.2, etc. represent the order in which the objects 402, 404A, 406A, 408A, 410A, etc. are called. This embodiment features a controller 402, and a fetch dispatcher 404A which dispatches fetch requests to different fetchers 406A and 406B, each using different modeling techniques to identify a set of candidate similar images from a data store. The fetch results are pooled in a pooler 410 and then sent via controller 402 to a score dispatcher 404B, which dispatches the query image and candidate set of similar images to scorers 408A and 408B, each using different modelling techniques to generate similarity scores. Notice fetch requests 3.1 and 3.2 can be computed in parallel, similarly for score requests 7.1 and 7.2.

Figure 7:
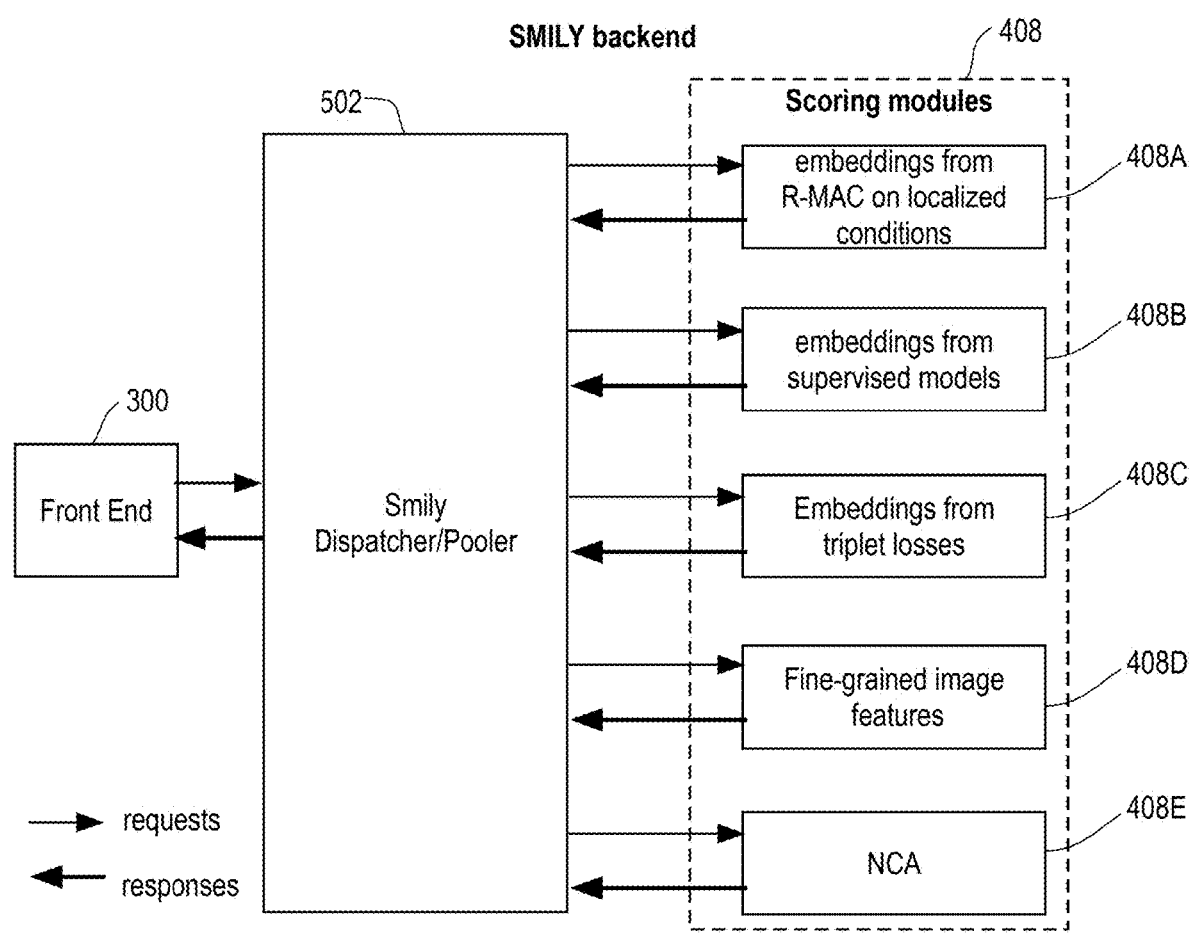
FIG. 7 is a block diagram of a portion of a back-end design showing a plurality of different scorers, each of which generate a similarity score between a query image and a set of candidate similar radiology images that captures diagnostic, visual and patient similarity attributes of the query image and the set of candidate similar radiology images including the annotations associated therewith.

FIG. 7 illustrates yet another configuration. A dispatcher/pooler 502 e.g., configured as per FIG. 5, forwards candidate images and the query image to each of 5 different scorers 408A, 408B, 408C, 408D and 408E in parallel. Each of the scorers uses a different modelling technique to generate the similarity score that captures similarity attributes of the query image and the set of candidate similar radiology images and their associated annotations, such as for example diagnostic, patient and visual similarity. Each scoring module generates a score using a distance metric based on an embedding or projection of a feature vector of the query image into a multidimensional space, e.g. shown in FIG. 11. Scoring module 408A uses embeddings from Regional Maximum Activations of Convolutions (R-MAC) on localized conditions. For further details see e.g. A Gordo et al., *Deep Image Retrieval: Learning global representations for image search*, arXiv.org [cs.CV] 1604.0132 (July 2016). Scoring module 408B uses embeddings obtained from supervised learning models. Scoring module 408C uses embeddings from triplet losses, explained below. Scoring module 408D uses embeddings from fine-grained image features, see. J. Wang, et al., *Learning fine-grained image similarity with deep ranking*, https://arxiv.org/abs/1404.4661 (2017). Scoring module 408E uses embeddings from a classifier with NCA (network component analysis).

Figure 11:
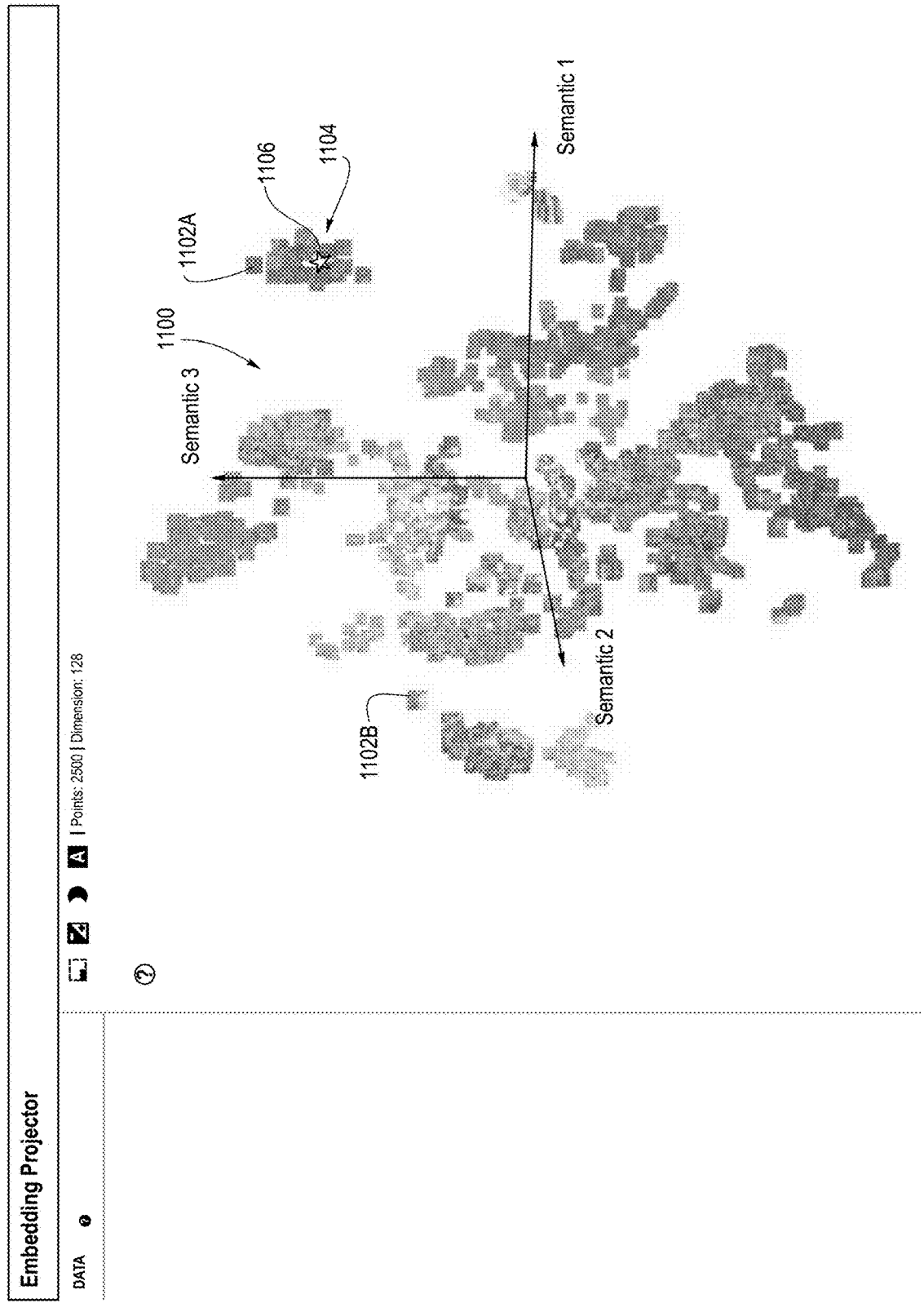
FIG. 11 is an illustration of a plot of an embedding of multitude of radiology images of the reference library in a multidimensional space. Each rectangular patch represents a single image in the reference library. The position of the images in the embedding is a factor of similarity in multiple axes.

FIG. 11 is an example of a plot of an embedding of multitude of candidate radiology images obtained from the reference library by the fetcher in a multidimensional space or embedding. For sake of ease of visualization of the embedding, the embedding consists of three axes. The axes represent different aspects of similarity, such as visual, diagnostic and patient. Each rectangular patch 1102A, 1102B, etc. represents a single radiology image. Images that are similar are clustered close to each other whereas dissimilar images are not. Similar medical images to a query image are found by projecting the query image feature vectors into the embedding of FIG. 4 scoring the neighboring images by distance in the multidimensional space. For example, referring to FIG. 11, the cluster of images 1104 containing image 1102A represents a group of images which are similar in all three axes to a query image 1106 indicated by the star. In this example, if the query image was a chest X-ray positive for pneumothorax, patient was a smoker, etc. the query image would be positioned in the location of the star 408 and the images in the cluster 1104 would be scored lower (i.e., more similar) than for example the image 1102B which is further away.

Having described the overall architecture and various possible configurations of the architecture in FIGS. 4, 5, 6 and 7, the fetchers, scorers and pooler will now be described in further detail.

Fetchers 406

As explained previously, the fetcher receives the query image and retrieves a set of candidate similar radiology images from a data store in the form of a library of ground truth annotated reference radiology images. The data store can be curated, i.e., developed and maintained, by obtaining ground truth annotated radiology images from publicly available or private sources, or by obtaining images from public or private sources and adding the ground truth annotations with the use of trained readers.

The fetcher can take the form of a trained deep convolutional neural network or classifier, optionally with filters, e.g. to exclude or include only some images for example those that are positive for a particular condition present in the query image. The fetcher can also include a function to first classify the query image (e.g., determine that it is positive for pneumothorax) and use that classification to filter the similar images to only those that have a ground truth annotation of pneumothorax. The fetcher could take several forms and could for example be configured in accordance with one of the following references, the content of which is incorporated by reference herein: C. Szegedy et al., *Going Deeper with Convolutions*, arXiv:1409.4842 [cs.CV] (September 2014); C. Szegedy et al., *Rethinking the Inception Architecture for Computer Vision*, arXiv:1512.00567 [cs.CV] (December 2015); see also US patent application of C. Szegedy et al., "Processing Images Using Deep Neural Networks", Ser. No. 14/839,452 filed Aug. 28, 2015. A fourth generation, known as Inception-v4 is considered as another possible architecture. See C. Szegedy et al., *Inception-v4, Inception-ResNet and the Impact of Residual Connections on Learning*, arXiv:1602.0761 [cs.CV] (February 2016). See also US patent application of C. Vanhoucke, "Image Classification Neural Networks", Ser. No. 15/395,530 filed Dec. 30, 2016, and PCT application serial no. PCT/US2017/019051 filed Feb. 23, 2017.

These candidate images may or may not already be associated with scores. For example, in one possible configuration, scores to similar images may be pre-assigned, and the fetcher may make use of pre-cached similar images to retrieve candidate similar images.

In one embodiment, one or more of the fetchers could be configured as a pre-cached fetcher. In a pre-cached fetcher, the similar candidate images for a given query image have been precomputed. The precomputing of similar images could be using any suitable technique.

The fetchers can use various different modelling techniques to determine similarity of images, and such modelling techniques are described in more detail in the discussion of the scorers. Such modelling techniques can include triplet loss, classification loss, regression loss and object detection loss.

Scorers 408

As noted above, the system uses one or more scorers which receive the query image and the set of candidate similar radiology images (identified by the fetcher) and generates a similarity score between the query image and each candidate image, using the image data as well as underlying annotations (image metadata, reports, patient information etc.) associated with the images. The score can be computed for example based on pre-computed embedding and a standard distance metric (e.g., cosine or Euclidean distance) in the embedding space. For example, the scorer looks up the embedding of an image in a database and then uses a distance measure in the embedding space. See the discussion of FIG. 11, supra.

The scorers implement a modelling technique to generate the similarity score that can capture similarity on many different axes (e.g., diagnostic, visual, patient, etc.) Diagnostic, visual and patient attributes are some of the many signals that could be important on specific axes of similarity, but these three are not meant to be an exhaustive list. A number of different modelling techniques are contemplated, and in a typical implementation where there are more than one scorer they will each use a different modelling technique that captures these different attributes of similarity (e.g., diagnostic, visual and patient).

In modeling similarity, one configuration of the scorers develops various signals in parallel that capture diagnostic, visual and patient similarity. The output from these signals will either be image embeddings that captures the similarity signal or a similarity score for every candidate image. The scoring module is responsible for combining the various signals and for the final scoring and ranking the candidate images. Some proposals for similarity models include the following:

Diagnostic Similarity (1) Utilize the corresponding report text based similarity to generate diagnostic similarity image triples. For instance, utilize the natural language processing (NLP) report extraction embeddings to capture report similarity and the images corresponding to these reports give us training for diagnostic image similarity. Since the similarity is based on the entire content of the radiology report these examples will capture all diagnostic conditions and not focus on a subset.

(2) Utilize the embeddings from existing X-ray classification models built for conditions like nodules, pneumothorax, opacity, etc. These are reasonably well-performing models and a similarity based on the top few layers of these models should capture diagnostic similarity.

Diagnostic+Location Similarity (1) Use a patch detection approach to identify small abnormalities (e.g., nodules) along with their locations. Given an input image with a small abnormality, automatically identify the abnormality and its location, and retrieve images with similar abnormalities at similar locations, highlighting the abnormalities in both input and retrieved images.

(1) Retrain a classifier (e.g., see J. Wang et al., *Learning Fine-grained Image Similarity with Deep Ranking*, arXiv: 1404.4661 [cs.CV] (2014)) using patch based image triples from a training image data set. A scoring schema could be as follows: Same abnormality from same location>same abnormality from a different location>different abnormality from the same location>all others.

Demographic and Patient Similarity (1) Models to identify if two X-rays belong to same person or not. A data set that includes longitudinal X-rays of a given patient gives us multiple images for the same person over time; use this to build a training set of same person vs not same person and the models can be trained over pairs or triplets to classify same person or not.

(2) Generate demographic similarity triplets using the fields in the a training data set person table like age, gender, ethnicity, smoking history, BMI (body mass index), height, weight, etc. Derive with heuristics for how to rank these characteristics to generate the training data.

Visual Similarity (1) Use a deep CNN image classifier such as that described in the J. Wang et al., *Learning Fine-grained Image Similarity with Deep Ranking paper*, supra. Or use the classifier with NCA (network component analysis) for feature selection using the X-ray data.

(2) Retrain the classifier of (1) using triples generated for demographic, patient and diagnostic similarity.

Abnormality Similarity (1) Train a Normal vs Abnormal image classifier. Use or develop a training data set that provides abnormal labels and is comprehensive. In one configuration, one can build a report extractor for normal vs abnormal from free text reports in the annotations and uses the corresponding images to generate the classifier.

(2) Cycle generative adversarial networks (GANs) to identify abnormal regions. Generate an abnormality vector for each image in a training data set with abnormality type and one of 16 abnormality locations. Train a classifier for pairs of images that predicts abnormality vector similarity effectively making images with the abnormalities in the same location more similar.

Figure 1B:
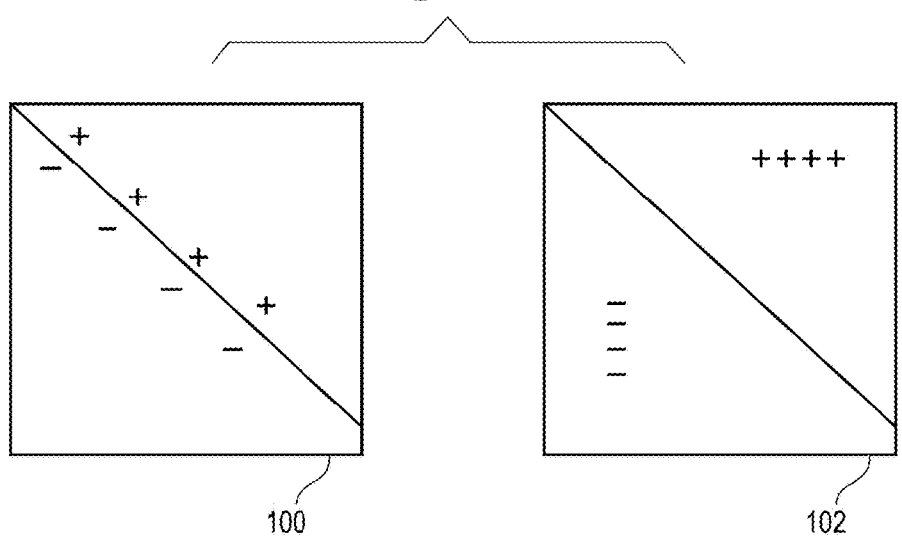
FIG. 1B is an illustration of classifications of positive and negative examples by two different classifiers.

As noted above in the discussion of FIG. 1B, training classifiers in and of itself is not sufficient to guarantee a good similarity metric, and we have a heterogeneous set of annotations in both the query image and in the set of candidate images retrieved by the fetchers. In a preferred configuration we use a number of different modeling techniques to generate similarity scores. We present a few of the techniques below. These include (a) triplet loss, which only requires some notion of ordering of images, thereby allowing us to deal with irregularly sampled data, hierarchy, and heterogeneous annotations/metadata; (b) regression loss, i.e., regressing to report embeddings, which is one technique that allows us to combine the modalities of image and report data; (c) classification loss, and (d) object detection loss, e.g., through the use of attention models, which takes into account the additional regional information within an image, which allows us to consider one additional layer of hierarchy of the regions of interest within an image, i.e. sub-image level metadata.

Triplet Loss

This is a technique, described in the literature, that allows us to handle our heterogeneous data consistently in a way that notionally captures similarity. Specifically, suppose we have three images: a query image and two candidate images. If we know that we have a query image that is closer to one of the candidate images (the positive) than it is to the other (the negative), then we expect the distance between the extracted features between the positive pair (query and positive candidate) to be smaller than the distance between the query and negative candidate. The triplet loss is thus the difference between these two distances. Thus, triplet losses are a way of comparing images by creating an ordering of some of the images, e.g. for a distance function D(.,.), saying that D(queryImage, image1)<D(queryImage, image2)

Any notion of distance can be turned into a triplet loss. The Hamming Distance is one way to construct such an ordering, by saying that images that have more of the same conditions (similar medical conditions, similar demographic information, localizable abnormalities appear in the same region, etc.) are more similar than those that have fewer.

More formally, we can encapsulate an evaluation metric as a distance function $$d(u, v) = \left\{ \sum_{c \in \{conditions\}} d_H(\rho(c, u), \rho(c, v)) \right\} + \left\{ \frac{1}{|\{image\ regions\}| + 1} \right.$$

$$\left. \sum_{r \in \{image\ regions\}} \sum_{c \in \{localizable\ conditions\}} d_H(\pi(r, c, u), \pi(r, c, v)) \right\}$$

where
$d_H(\bullet, \bullet)$ is the Hamming distance
$\rho\ (\bullet, \bullet)$: {conditions}×{images}→{0, 1}
$\rho\ (c, u)=1$ iff image u exhibits the condition c in the image.

π (•, •, •) {image region}×{localizable conditions}×{images}→{0, 1}

π (r, c, u)=1 iff image u exhibits condition c in region r. Here, condition is used loosely to capture both medical abnormalities as well as demographic information.

We say an image t is more similar to image v if
d(t, u)<d(t, v)

The Hamming Distance is not the only way to construct such an ordering. Some alternatives include:

a) Images taken of the same patient that are closer in time are more similar than images taken of the same patient that are farther apart b) A medical practitioner provides their own subjective ordering of some of the images c) Chest X-Ray images with an associated radiology report text, projected to a common embedding space, are more similar to each other than the original X-ray with a radiology report associated with a different Chest X-ray image.

d) Chest X-Ray images with a follow-up chest CT, projected to a common embedding space, are more similar to each other than the original chest X-Ray with a chest CT that followed up a different Chest X-ray.

e) All permutations of c) and d) swapping the positions of radiology report, Chest X-Ray, and chest CT.

Classification Loss

There are other methods for modelling similarity as alternative to triplet loss. One is classification loss. Specifically, we could directly train classifiers for certain conditions. Classification loss can take several forms. One is cross-entropy loss, or log loss, which measures the performance of a classification model whose output is a probability value between 0 and 1. Cross-entropy loss increases as the predicted probability diverges from the actual label. The details are known in the art and described in the literature, for example in the tutorial http://ml-cheatsheet.readthedocs.io/en/latest/loss_functions.html.

Regression Loss

This is another alternative to the triplet loss technique. If we have an embedding for an associated image modality, e.g. a radiology report associated with a chest X-Ray or a chest CT associated with the same chest X-ray, we can formulate it as a regression problem. The idea here is to predict the report embedding vector directly from the image, modeling it as a regression problem. To the extent the report embedding accurately captures similarity, then a good regression model on the image would also capture similarity.

The simplest notion of regression is one-dimensional linear regression, which corresponds to finding the slope and intercept so that one can map an input feature to an output value, e.g.

$y=mx+b$, where given examples of $(x\_i, y\_i)$ pairs, we find the slope m and intercept be that would minimize for some loss, e.g. squared error:

$\min\_{m,b} \sum\_i (y\_i-(mx\_i+b))^2$

We can generalize this idea if we have some function $f$ to extract features from a report as well as another function g to extract features from an image. The outputs could be vectors, so there could be an equation $f(report)=Mg(image)+b$, where $M$ is a matrix, and $b$ is a vector.

Furthermore, if g is a neural network, we can not only adjust the value of M and b for fixed $f$ and g, but also update the value of g over time as well. If the output dimension of g is the same as that of $f$, it turns out that this is equivalent to making M an identity matrix and b a zero vector, so given example pairs (report_i, image_i), we can solve a regression problem by minimizing for some loss, e.g. squared error: $\min\_{g} \sum\_i (f(report\_i)-g(image\_i))^2$.

Object Detection Loss

Object detection loss is another modelling technique for capturing similarity. One might note that if a pneumothorax is found in the same part of a candidate image as the query, those images might be closer to one another. If the existence, size, or location of elements within an image are important for determining similarity, e.g. the position of the carina and the tip of an ET tube to determine whether the ET tube is correctly placed, or the location and size of a pulmonary nodule, then we can formulate it as an object detection problem (object detection loss, e.g. intersection over union).

Therefore, if one knows where in an image a condition is, that could be used to model similarity. Attention mechanisms give us the capability to do this. The technique of Integrated Gradients can be used, as an example of an attention mechanism. Attention mechanisms, such as Integrated Gradients, are machine learning tools which basically identify those portions of the data set that contribute the most to the model predictions. These portions of the X-ray or CT scan data set can then be highlighted by adding bounding boxes in the images enclosing abnormal tissue or tumors identified from the attention mechanism. The Integrated Gradients algorithm is described in the paper of M. Sundararajan et al., *Axiomatic Attribution for Deep Networks*, arXiv:1703.01365 [cs.LG] (June 2017), the entire content of which is incorporated by reference. The methodology will be described conceptually in the context of attribution of individual pixels in an image in a classification of the overall image. Basically, an Integrated Gradients score $IG_i$ (or attribution weight or value) for each pixel i in the image is calculated over a uniform scaling ($\alpha$) of the input image information content (spectrum of brightness in this example) from a baseline (zero information, every pixel black, $\alpha=0$), to the full information in the input image ($\alpha=1$), where $IG_i$ (score for each pixel) is given by equation (1)

$$IG_i(image)=image_i * \int_{0-1} \nabla F_i(\alpha * image) d\alpha \qquad (1)$$

where F is a prediction function for the label;
$image_i$ is the RGB intensity of the ith pixel;
$IG_i$(image) is the integrated gradient w.r.t. the $i_{th}$ pixel, i.e., attribution for $i_{th}$ pixel; and
$\nabla$ is the gradients operator with respect to $image_i$.

Section 3 of the Sundararajan et al. paper explain the algorithm further and that description is incorporated by reference.

The use of attention mechanisms in deep learning neural networks is described in the conference presentation of D. Bandanau et al., *Neural Machine Translation by Jointly Learning to Align and Translate*, January 2014 (arXiv: 1409.0473[cs.CL]. Further explanations of attention mechanisms in the context of healthcare include Choi et al., GRAM: *Graph-based attention model for Healthcare Representation Learning*, arXiv:1611.07012v3 [cs.LG] April 2017 and Choi et al., *RETAIN: an Interpretable Predictive Model for Healthcare using Reverse Time Attention Mechanism*, arXiv:1608.05745v3[cs.GL] February 2017.

The goal here is not only to use where in the image something occurs to inform similarity. There are several techniques to explain what components (pixels) in the image contribute the most to model prediction, including the techniques of soft attention and integrated gradients discussed above. One can also explicitly capture, through the assistance of labelers marking the images, where in an image a specific item is, e.g. the location of a carina, which is in the same vein as c) in the above alternative to triplet losses, i.e. object detection problems.

Our framework of fetchers, scorers, and poolers allows us to seamlessly combine techniques that can use any or all of these different losses and distance methods.

Pooler 410 and Ranking

As noted above, the system of FIGS. 4-7 further includes a pooler 410 which receives the similarity scores from the one or more scorers 408, ranks the candidate images (e.g., on the basis of acuteness/severity), and returns a list of the candidate images reflecting the ranking. The pooler 410 thus pools and ranks the candidate images based on scores from the different scorers 408.

In one configuration, a final ranking is done at the pooler 410, with intermediate rankings proposed by the scorers, e.g., based on the similarity scores. There can also be an implicit exclusion of certain images from the ranking based on the candidate set of images that are returned by the fetcher(s) 406.

The final ranking can be a mix of objective measures like the Hamming distance and scores derived from subjective measures, e.g., what medical professionals actually consider to be similar images for the clinical context they are working in. Subjective measures could be used for a final comparison of different models or ranking methods. For instance, consider a set of query images $q\_1, \ldots, q\_N$, and for each of these queries, we receive ranked images $r\_1(q\_i)$, $r\_2(q\_i), \ldots, r\_k(q\_i)$ the top k images returned for query image $q\_i$. Then, doctors and/or other medical professionals, could indicate whether the ordering of $r\_1(q\_i)$, $r\_2(q\_i), \ldots, r\_k(q\_i)$ makes sense for image $q\_i$ and how relevant they are. From these, one could compute scores for image pairs $q\_i, r\_1(q\_i))$ $q\_i, r\_2(q\_i)$

...

$q\_i, r\_k(q\_i)$

As we collect more of these labels and we generate/evaluate different ranking methods, we can rate how well the ranking method does based on the scores collected above, so it offers a way to compare different ranking methods against one another.

There are several options for the final ranking:

Option 1—Logistic Regression Model with Weighted Sum of Scores

This option might fail to capture certain nonlinearities in when and how to weight the different scores from the scorers.

Option 2 Generalized Additive Models

This option offers a framework for combining features together from different scoring components. Generalized additive models are a generalized linear model in which the linear predictor depends linearly on unknown smooth functions of some predictor variables, and interest focuses on inference about these smooth functions. They are described in the scientific and technical literature, see for example the explanation at https://en.wikipedia.org/wiki/Generalized_additive_model, therefore a detailed description is omitted for the sake of brevity.

Option 3—Neural Network Based on Scores as Inputs.

As a general matter, here are a number of techniques that could be used to compute a final ranking, from a simple heuristic, e.g. taking the harmonic mean of the intermediate rankings produced by each scorer, to something more sophisticated like training a model to use a weighted approximate pairwise (WARP) loss. See for example the conference paper of J. Weston et al., *Learning to Rank Recommendations with the k-Order Statistic Loss*, RecSys'13, Oct. 12-16, 2013, Hong Kong, China, available on-line at https://research.google.com/pubs/archive/41534.pdf Example User Interfaces As explained in FIG. 3, once the similar images are retrieved, scored and ranked, they are presented to the user. The information that is returned to a user includes not just the similar images (and associated annotations, e.g. metadata, reports or excerpts thereof), but also information that can be culled, inferred or aggregated from the result set of the similar images, such as the statistics that can be computed from the query images. Several examples are as follows.

1) The images can be returned not merely as a list of images but rather grouped together across common attributes that are useful for supporting a clinical decision. For example, in FIG. 8 there is shown a display on a workstation showing the query image 202 and the results 204, in the form of a multitude of similar images 304. The similar images 304 are grouped in rows, with a legend in the form of a diagnosis or fining associated with each row. Row 802, NGT (nasogastric tube) Correctly Placed, has a set of four images 304 that have that characterization. Row 804 has a legend Pneumonia. Row 806 has a legend Pneumothorax. Thus, in this example, images with correctly placed foreign bodies (e.g., nasogastric tube) are grouped separately from those images that are associated with a diagnosis of pneumothorax and diagnosis of pneumonia.

2) The groupings can involve the aggregation of relevant common text from radiology free text reports. For example, while there may not be a specific label indicating that an endotracheal tube is misplaced, we can aggregate together images that are associated with reports having common phrases that imply this condition to be present, for example reports having text entries "endotracheal tube at the level of the carina", "endotracheal tube tip terminates in right main bronchus", or "ET tube tip could be advanced a couple of centimeters for standard positioning." Attention mechanisms in the scorers can be used to identify portions of the free text reports, such as particular words or phrases, which contribute the most to the similarity score.

3) When we group by these common phrases in reports (or by the presence or absence of enumerated conditions in other metadata), as in example 2) above, we can aggregate these into values and compare them against a baseline, and report the comparison. For example, the similar image results are 100 images, and we may report that fact that 60 of the 100 images indicated pneumothorax was present, even though only 1 of every 1000 images in the reference library database contain pneumothorax.

Figure 8:
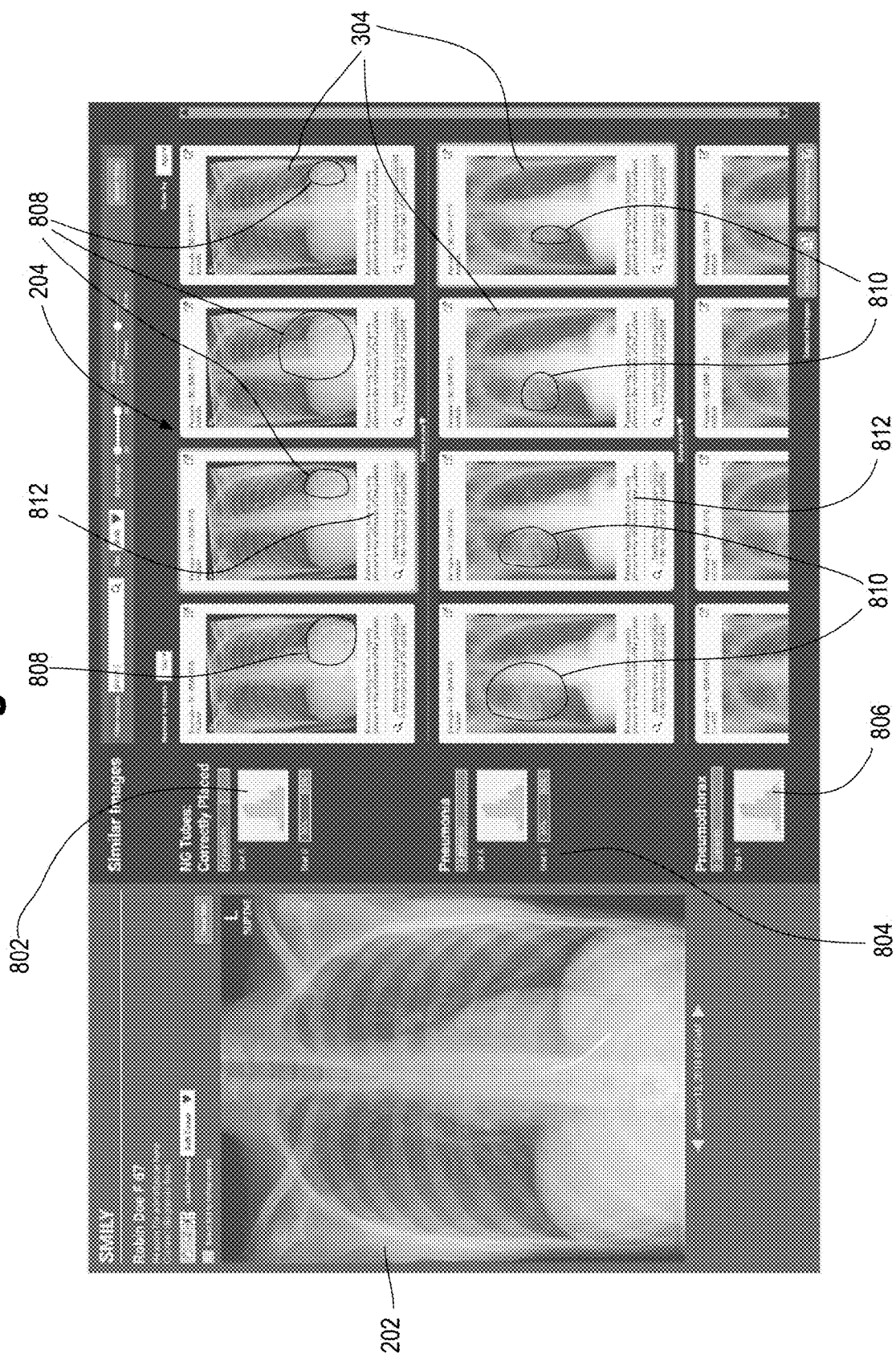
FIG. 8 is an illustration of a display on a workstation used by the medical professional showing a query image and a set of similar radiology images retrieved, scored and ranked using the back-end design of FIG. 4, 5, 6, or 7, as well as aggregated information from the set of similar radiology images in which the retrieved images are sorted or group by diagnosis.

FIG. 8 also illustrates the use of attention mechanism in the models used by the scoring module. For the top row 802 of images with the legend "NG tubes correctly placed", the circles 808 indicate areas (patches of pixels) of the chest X-rays, with NG tubes placed correctly, which are colored with a contrasting color, e.g., red, to illustrate the areas in the image that the model weighted most heavily to generate a high score of similarity to the query image for this diagnosis.

Similarly, the circles 810 illustrate regions in the X-ray images in the "Pneumonia" row of images which are shown in a contrasting color to illustrate those patches or areas in the image that the model weighted most heavily to generate a high score of similarity to the query image for this diagnosis. The row of images 806 for Pneumothorax diagnosis has similar areas which are highlighted to indicate the greatest weight by the model. The attention models can also be applied to annotations associated with the similar images, such as the free text in the radiology reports associated with the images, and in FIG. 8 the free text areas 812 below the images there can be words or phrases from the annotations highlighted to indicate that the attention model gave significant weight to such words or phrases in determining similarity to the query image.

Figure 9:
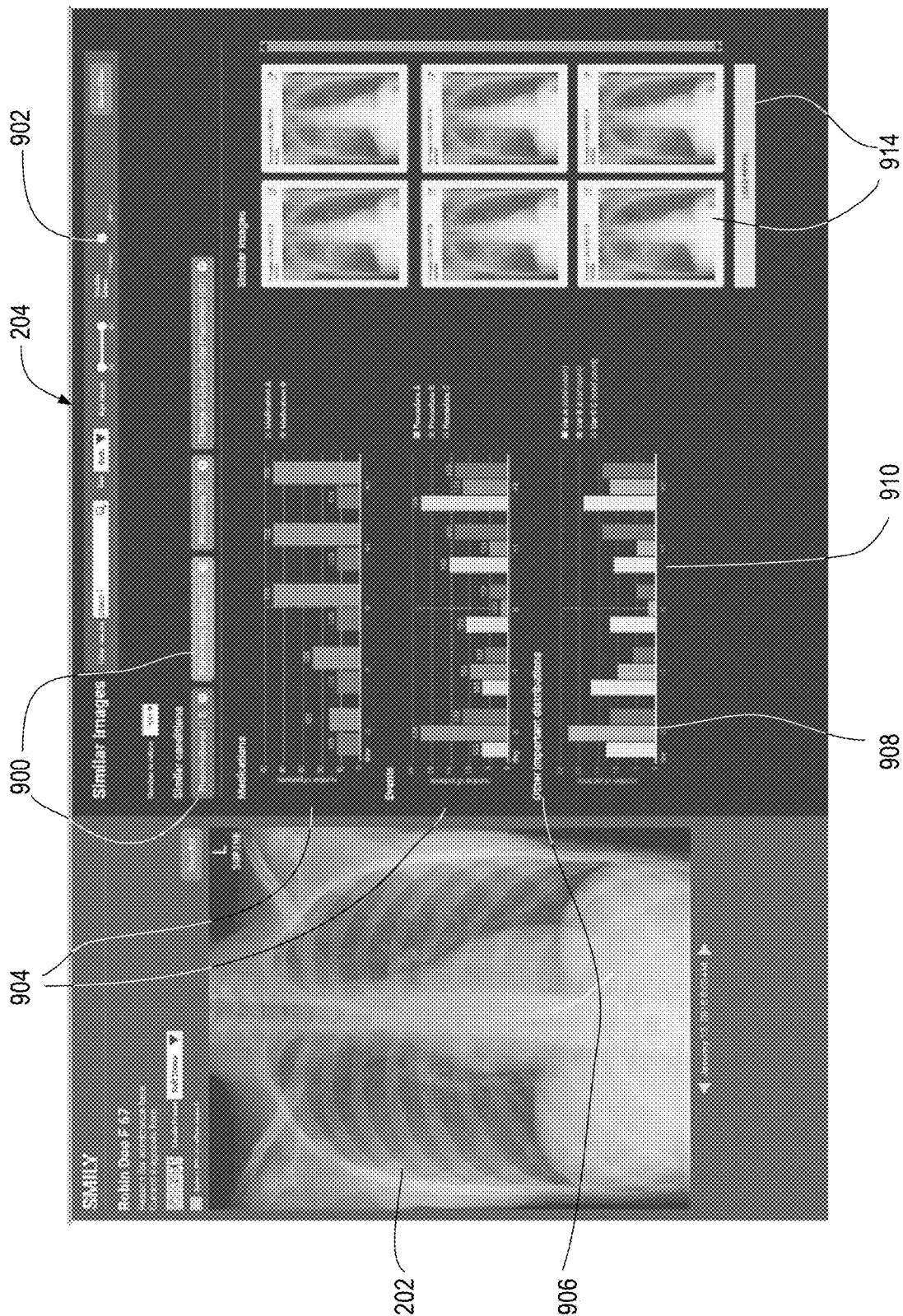
FIG. 9 is an illustration of a display on a workstation showing a query image, a set of retrieved similar medical images, and a set of statistical plots showing various statistics associated with the retrieved similar images, such as the medications received, the occurrence of certain medical events over a period of days, and so forth.

FIG. 9 is an illustration of another display of a query image 202 and the results 204. This configuration emphasizes summarizing similar patient data over time, but still provides individual instances of similar images. The horizontal bars 900 identify similar conditions, with the counts (numbers) of similar images that were returned. For example, the first bar has a condition "pneumothorax" and a count of 13, the second bar has a condition of "pulmonary embolism" and a count of 31. The bar 902 on the right hand has a condition "change in line or tube placement" and an option (X) to remove the condition if it is not relevant to the diagnosis of the query image. The region 904 shows summary statics on a timeline for similar patients. This timeline shows what medications/events happened for similar patients before and after the most similar image. The trends in the timelines may highlight obvious interventions to make for the patient associated with the query image. The region 906 shows plots of other significant distributions. Gradual trends may indicate that correct diagnoses were initially missed, suggesting it could be useful to carefully consider this patient's case. The bars 908 can be clicked in which case a filtering operation occurs which filters the similar images to only those represented in that selected bar. Other aggregate statistics are shown in the region 910. The area 912 shows the most similar images to the query image. A load more icon 914 allows the user to load more images and a scroll bar allows the user to navigate down to the newly loaded images.

Figure 10:
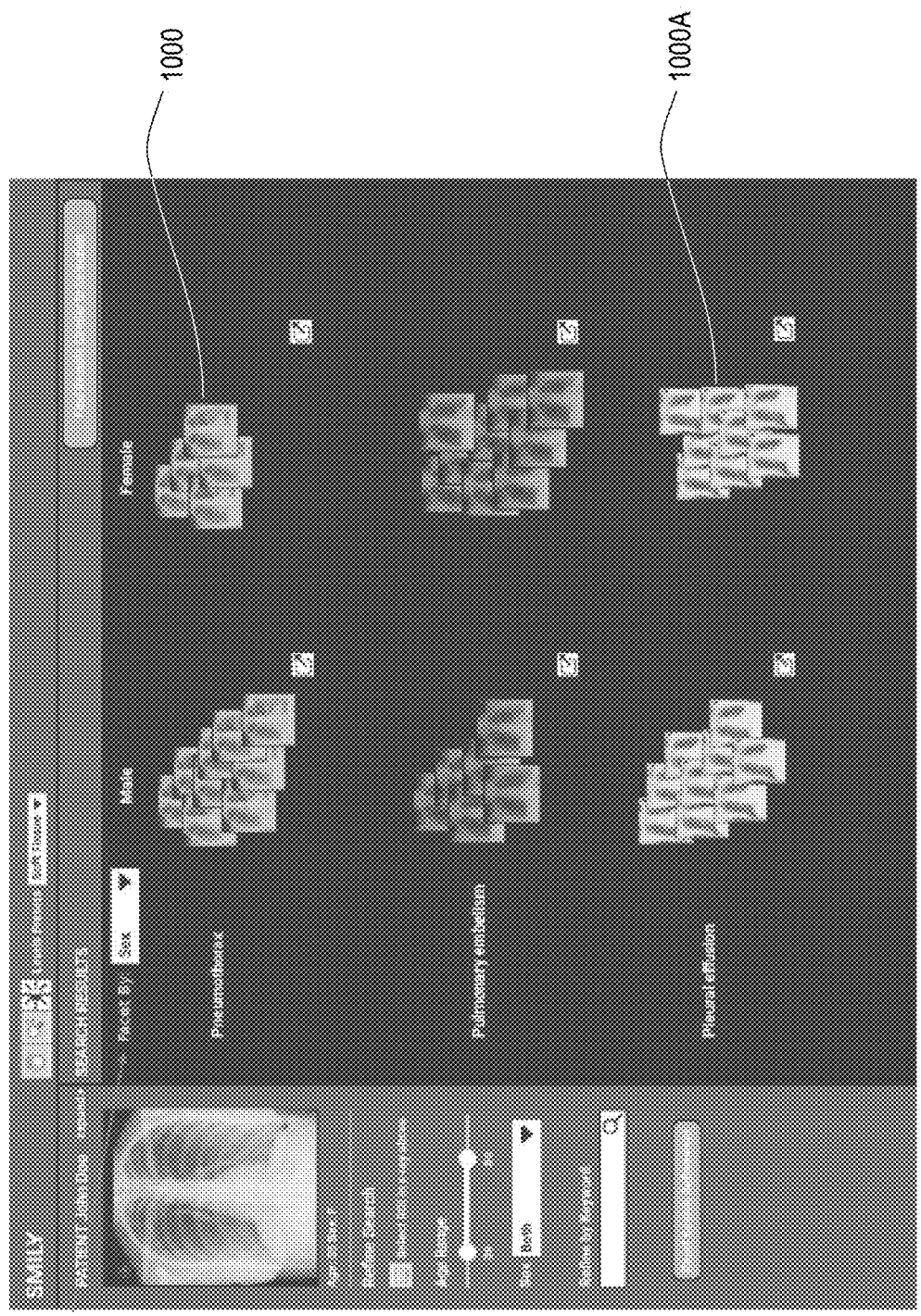
FIG. 10 is an illustration of a display on a workstation showing a query image, and thumbnail images of retrieved similar images and showing the distribution of the similar images, in this case grouping by sex (left and right columns) and diagnosis (rows).

FIG. 10 shows another alternative display in which the similar images are grouped or clustered by diagnosis (rows) and by patient sex (columns). The number of thumbnail images in each cluster 1000 reflects either directly or proportionately the number of similar images that were returned. A user can select a cluster, e.g., female, plural infusion, cluster 1000A, and the similar images in that cluster are displayed, e.g., as shown in FIG. 3 or FIG. 8.

In summary, once the set of similar images have been identified, relevant information is returned to the user from this set. This would normally include not only the images themselves, but also metadata associated with each of these images like radiology reports, clinical decisions made (e.g., prescribing of antibiotics, diuretics), classification diseases/conditions associated with the similar image, an information relating to a grouping/aggregation of these results. That aggregation could include clustering together image results with similar properties, generating pivot tables summarizing the prevalence of certain conditions/diagnoses in the images, as well as indicating the prevalence of common phrases within the radiology reports.

The system of this disclosure could be deployed in a cloud environment in which the back end of FIGS. 4-7 is implemented remotely (e.g., in the cloud, for example by a service provider that trained and developed the deep learning models used to fetch, score and rank similar images and curated the reference library of ground truth annotated radiology images). In this configuration, a query image set is sent over a computer network (e.g., the Internet) and the service provider returns the candidate similar images, with ranking, aggregated information, annotations, etc., to a front end implemented in a medical clinic, hospital or office where the query image was obtained, where a radiologist is considering the query image, or where a physician may be consulting with a patient in regards to the query image and planning further treatment. Alternatively, the system of this disclosure could be implemented locally, i.e., with the back end and associated computing resources, reference library, software modules and deep learning models located locally to the office, clinic, or hospital where the query image is obtained, or viewed on a workstation e.g. by a radiologist or a primary care physician.

We claim:

1. A computer-implemented system for identifying clinically useful similar radiology images to a query image, comprising:
   one or more fetchers receiving the query image and retrieving a set of candidate similar radiology images from a data store;
   one or more scorers receiving the query image and the set of candidate similar radiology images and generating a similarity score between the query image and each candidate image; and
   a pooler receiving the similarity scores from the one or more scorers, ranking the candidate images, and returning a list of the candidate images reflecting the ranking,
   wherein the one or more scorers implement a modelling technique to generate the similarity score capturing a plurality of similarity attributes of the query image and the set of candidate similar radiology images and annotations associated therewith,
   wherein the attributes of the query image and the set of candidate similar radiology images captured by the similarity score including diagnostic, visual, and patient demographic attributes, and
   wherein:
   (i) the system further includes a processing unit which aggregates information from the annotations associated with the set of candidate similar radiology images, the annotations comprise text-based radiology reports, and the processing unit groups images in the set of candidate similar radiology images by relevant common text from text-based radiology reports; or
   (ii) the system further includes the processing unit which aggregates information from the annotations associated with the set of candidate similar radiology images and the processing unit groups images in the set of candidate similar radiology images by the presence or absence of enumerated conditions in the annotations; or
   (iii) the modelling technique implemented in the one or more scorers is trained to determine whether the query image is from the same patient as each candidate image using a data set that includes images of a single patient over time.

2. The system of claim 1, wherein the one or more fetchers implement a modelling technique capturing a plurality of attributes of the query image and the set of candidate similar radiology images and annotations associated therewith to retrieve the set of candidate similar radiology images.

3. The system of claim 2, wherein the modelling technique implemented in the one or more fetchers comprises triplet loss, classification loss, regression loss, or object detection loss.

4. The system of claim 2, wherein there are at least two fetchers and each uses a different modelling technique.

5. The system of claim 2, wherein there are at least two scorers and each uses a different modelling technique.

6. The system of claim 1, wherein the modelling technique implemented in the one or more scorers comprises triplet loss, classification loss, regression loss, or object detection loss.

7. The system of claim 1, wherein the pooler ranks the candidate images using a logistic regression model with weighted sum of scores.

8. The system of claim 1, wherein the pooler ranks the candidate images using a generalized additive model.

9. The system of claim 1, wherein the pooler ranks the candidate images using a neural network based on scores as input.

10. The system of claim 1, wherein the system further includes the processing unit which aggregates information from the annotations associated with the set of candidate similar radiology images.

11. The system of claim 10, wherein the processing unit groups images in the set of candidate similar radiology images across common attributes that are useful for supporting a clinical decision.

12. The system of claim 10, wherein the annotations comprise text-based radiology reports, and wherein the processing unit groups images in the set of candidate similar radiology images by relevant common text from text-based radiology reports.

13. The system of claim 12, wherein the processing unit aggregates the groupings into numerical values and a comparison of the numerical values to a baseline.

14. The system of claim 10, wherein the processing unit groups images in the set of candidate similar radiology images by the presence or absence of enumerated conditions in the annotations.

15. The system of claim 1, further comprising a front end in the form of a workstation configured to display the query image, the candidate similar radiology images, and metadata associated with each of the candidate similar radiology images.

16. The system of claim 15, wherein the metadata comprises radiology reports or excerpts thereof, clinical decisions made, classification of diseases or conditions associated with the similar radiology image, or information relating to a grouping or aggregation of data associated with the candidate similar radiology images.

17. The system of claim 1, wherein the modelling technique implemented in the one or more scorers is trained to determine whether the query image is from the same patient as each candidate image using the data set that includes images of the single patient over time.

18. The system of claim 1, wherein the patient demographic attributes comprise an age, a gender, an ethnicity, a smoking history, a body mass index, a height, or a weight.

19. A method for identifying and retrieving clinically useful similar radiology images to a query radiology image, the query image associated with annotations including metadata, comprising:
curating a data store of ground truth annotated radiology images, each of the radiology images associated with annotations including metadata;
receiving the query image and retrieving a set of candidate similar radiology images from the data store; and
generating a similarity score between the query image and each candidate similar radiology image using at least two different scoring modules,
wherein the at least two scoring modules implement a different modelling technique to generate the similarity score capturing a plurality of similarity attributes of the query image and the set of candidate similar radiology images and the annotations associated therewith,
wherein the attributes of the query image and the set of candidate similar radiology images captured by the similarity score includes diagnostic, visual, and patient demographic attributes, and
wherein:
(i) the method further comprises:
aggregating, by a processing unit, information from the annotations associated with the set of candidate similar radiology images, wherein the annotations comprise text-based radiology reports; and
grouping, by the processing unit, images in the set of candidate similar radiology images by relevant common text from text-based radiology reports; or
(ii) the method further comprises:
aggregating, by the processing unit, information from the annotations associated with the set of candidate similar radiology images; and
grouping, by the processing unit, images in the set of candidate similar radiology images by the presence or absence of enumerated conditions in the annotations; or
(iii) at least one of the two different scoring modules comprises a modelling technique trained to determine whether the query image is from the same patient as each candidate image using a data set that includes images of a single patient over time.

20. The method of claim 19, further comprising:
ranking the candidate similar radiology images; and
returning a list of the candidate similar radiology images reflecting the ranking and aggregated information obtained from the annotations associated with the set of candidate similar radiology images.

21. The method of claim 20, wherein ranking the candidate similar radiology images comprises ranking the candidate similar radiology images using a logistic regression model with weighted sum of scores.

22. The method of claim 20, wherein ranking the candidate similar radiology images comprises ranking the candidate similar radiology images using a generalized additive model.

23. The method of claim 20, wherein ranking the candidate similar radiology images comprises ranking the candidate similar radiology images using a neural network based on similarity scores as input.

24. The method of claim 19, wherein receiving the query image and retrieving the set of candidate similar radiology images from the data store comprises implementing a modelling technique capturing a plurality of attributes of the query image and the set of candidate similar radiology images and annotations associated therewith to retrieve the set of candidate similar radiology images.

25. The method of claim 24, wherein the modelling technique comprises triplet loss, classification loss, regression loss, or object detection loss.

26. The method of claim 19, wherein the modelling techniques comprises triplet loss, classification loss, regression loss, or object detection loss.

\* \* \* \* \*